(12) United States Patent
Dutta et al.

(10) Patent No.: US 9,439,921 B2
(45) Date of Patent: *Sep. 13, 2016

(54) PHARMACEUTICAL FORMULATIONS COMPRISING HIGH PURITY CANGRELOR AND METHODS FOR PREPARING AND USING THE SAME

(71) Applicant: The Medicines Company, Parsippany, NJ (US)

(72) Inventors: Panna Dutta, Flemington, NJ (US); Adel Rafai Far, Mount-Royal (CA); Min Ding, Irvington, NY (US); Rajeshwar Motheram, Dayton, NJ (US)

(73) Assignee: THE MEDICINES COMPANY, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/049,727

(22) Filed: Feb. 22, 2016

(65) Prior Publication Data

US 2016/0199400 A1  Jul. 14, 2016

Related U.S. Application Data

(63) Continuation of application No. 14/796,368, filed on Jul. 10, 2015, now Pat. No. 9,295,687.

(60) Provisional application No. 62/103,136, filed on Jan. 14, 2015.

(51) Int. Cl.
*A61K 31/70* (2006.01)
*A61K 31/7076* (2006.01)
*A61K 47/10* (2006.01)

(52) U.S. Cl.
CPC ........... *A61K 31/7076* (2013.01); *A61K 47/10* (2013.01)

(58) Field of Classification Search
CPC ....................................................... A61K 31/70
USPC ........................................................... 514/47
See application file for complete search history.

(56) References Cited

U.S. PATENT DOCUMENTS

| | | |
|---|---|---|
| 5,721,219 A | 2/1998 | Ingall et al. |
| 5,955,447 A | 9/1999 | Ingall et al. |
| 6,114,313 A | 9/2000 | Bland et al. |
| 6,130,208 A | 10/2000 | Broadhead |
| 6,657,076 B1 | 12/2003 | Purdie |
| 7,674,790 B2 | 3/2010 | Ugwu et al. |
| 8,680,052 B1 | 3/2014 | Arculus-Meanwell et al. |
| 8,716,261 B2 | 5/2014 | Ruderman Chen et al. |
| 8,759,316 B2 | 6/2014 | Ruderman Chen et al. |
| 8,871,736 B2 | 10/2014 | Chen et al. |
| 9,295,687 B1 * | 3/2016 | Dutta ........................ A61J 1/00 |

OTHER PUBLICATIONS

Bansal et al.; Product Development Issues of Powders for Injection; Pharmaceutical Technology; Mar. 2002; pp. 122-132.

Tang et al.; Design of Freeze-Drying Processes for Pharmaceuticals; Practical Advice, Pharmaceutical Research; vol. 21; No. 2; Feb. 2004; pp. 191-200.

* cited by examiner

*Primary Examiner* — Raymond Henley, III
(74) *Attorney, Agent, or Firm* — Wenderoth, Lind & Ponack, L.L.P.

(57) ABSTRACT

The present invention relates to high purity cangrelor, pharmaceutical formulations comprising high purity cangrelor as an active ingredient, methods for preparing such compounds and formulations, and methods for using the pharmaceutical formulations in the inhibition of platelet activation and aggregation.

26 Claims, No Drawings

US 9,439,921 B2

PHARMACEUTICAL FORMULATIONS COMPRISING HIGH PURITY CANGRELOR AND METHODS FOR PREPARING AND USING THE SAME

CROSS-REFERENCED TO RELATED APPLICATIONS

The present application is a continuation of U.S. Ser. No. 14/796,368, filed Jul. 10, 2015, now U.S. Pat. No. 9,295,687, which claims benefit of U.S. Ser. No. 62/103,136, filed Jan. 14, 2015.

FIELD OF THE INVENTION

The present invention is generally directed towards pharmaceutical formulations comprising high purity cangrelor or one or more salts thereof as an active ingredient, to methods for preparing such pharmaceutical formulations where low levels of impurities are consistently achieved and maintained, and to methods for using the pharmaceutical formulations in the inhibition of platelet activation and aggregation.

BACKGROUND OF THE INVENTION

The inhibition of platelet activation and aggregation, or antiplatelet therapy, has been recognized as a means to impact coagulation and inflammation in a way that conventional anticoagulant therapy is unable to (Bhatt, D. L.; Topol, E. J. *Nat Rev Drug Disc* 2003, 2, 15-28). As such, inhibitors of platelet activation and aggregation are substances that are useful during percutaneous coronary intervention (PCI) and other catherization techniques in order to reduce bleeding complications, and in the treatment of acute coronary syndromes (ACS) and clotting disorders in general. One class of antiplatelet agents is inhibitors of the $P2Y_{12}$ receptor, a G-protein coupled purinergic receptor which is an important component of platelet activation (Dorsam, R. T.; Kunapuli, S. P. *J Clin Invest* 2003, 113, 340-345). In particular, cangrelor ([dichloro-[[[(2R,3S,4R,5R)-3,4-dihydroxy-5-[6-(2-methylsulfanylethylamino)-2-(3,3,3-trifluoropropylsulfanyl)purin-9-yl]oxolan-2-yl]methoxy-hydroxyphosphoryl]oxy-hydroxyphosphoryl]methyl]phosphonic acid; the mixed mono(anhydride) of N-[2-(methylthio)ethyl]-2-[(3,3,3-trifluoropropyl)thio]-5'-adenylic acid with dichloromethylenebisphosphonic acid) is a reversible inhibitor of the $P2Y_{12}$ receptor which is under clinical evaluation for its potential use in PCI.

Cangrelor (also referred to as ARC69931MX) is a synthetic analogue of adenosine triphosphate (ATP) and a potent antagonist of the $P2Y_{12}$ receptor with a $pIC_{50}$ of 9.35 (Chattaraj, S. C. *Curr Opin Investig Drugs* 2001, 2, 250-55; Diaz-Ricart, M. *Drugs Future* 2008, 33, 101-110; U.S. Pat. No. 5,721,219 and U.S. Pat. No. 5,955,447). It is being developed as the sodium salt.

In light of the medical and therapeutic applications of cangrelor, it is essential that pharmaceutical formulations comprising cangrelor maintain high levels of purity. Formulations comprising cangrelor are compounded formulations, e.g., cangrelor undergoes a compounding process following its synthesis so that it is usable and stable for medical and therapeutic applications. This compounding process typically includes mixing the drug with excipients in a solution, followed by aseptic filtration and lyophilization.

Impurities such as, but not exclusively, dichloromethylenebisphosphonic acid, N-[2-(methylthio)ethyl]-2-[(3,3,3-trifluoropropyl)thio]-5'-adenylic acid (a product of the hydrolysis of the dichloromethylenebisphosphonate group on cangrelor), its bis(anhydride) with dichloromethylenebisphosphonic acid, N-[2-(methylsulfinyl)ethyl]-2-[(3,3,3-trifluoropropyl)thio]-5'-adenylic acid monoanhydride with dichloromethylenebisphosphonic acid and 2-(3,3,3-trifluoropropylthio)-N-(2-(methylthio)ethyl)-adenine and others may be generated during the synthesis and the compounding process. These compounds are represented in their neutral form but are generally present as salts.

Methods have been developed that minimize the generation of impurities during cangrelor synthesis. However, impurities produced during the compounding process remain problematic. It has been shown that various compounding processes can result in formulations in which a significant proportion of cangrelor has been degraded, which may affect not only product stability and shelf-life, but ultimately the ability to control dosage during administration to patients. In addition, because the pharmacological impact of the degradation products has not been evaluated in clinical settings, it is critical to maintain them to a level at or below the levels used in clinical evaluation. Therefore, development of a compounding process for formulating cangrelor that consistently generates formulations having low levels of impurities is desirable.

The invention disclosed herein addresses the need for pharmaceutical formulations comprising high purity cangrelor as the active ingredient and methods for producing the same, where low levels of impurities are consistently achieved and maintained.

SUMMARY OF THE INVENTION

The present invention relates to (i) high purity cangrelor, or one or more salts thereof, (ii) pharmaceutical formulations comprising high purity cangrelor, or one or more salts thereof, as an active ingredient and one or more pharmaceutically acceptable excipients, (iii) methods for preparing such compounds and formulations, and (iv) methods for using compounds and the pharmaceutical formulations in the inhibition of platelet activation and aggregation.

Thus in one embodiment, the invention relates to high purity cangrelor, or a salt thereof. High purity cangrelor is cangrelor having a combined total of selected hydrolysis and oxidation degradants of cangrelor not exceeding about 1.5% by weight of the high purity cangrelor (i.e., high purity cangrelor includes (i) cangrelor and (ii) selected hydrolysis and oxidation degradants of cangrelor not exceeding about 1.5% by weight of the combination of the cangrelor and the degradants). Selected hydrolysis and oxidation degradants of cangrelor are impurity A, impurity B, impurity C, impurity D and impurity E. Thus, in one aspect of this embodiment, high purity cangrelor of the present invention has a combined impurity level of impurities A, B, C, D and E of less than about 1.5% by weight of the high purity cangrelor. In other aspects, high purity cangrelor of the present invention has a combined impurity level of impurities A, B, C, D and E of less than about 1.4% by weight, less than about 1.3% by weight, less than about 1.2% by weight or less than about 1.0% by weight. In another aspect, the amount of impurity A present in the high purity cangrelor is less than about 0.5% by weight, and/or the amount of impurity B present in the high purity cangrelor is less than about 0.2% by weight, and/or the amount of impurity C present in the high purity cangrelor is less than about 0.3% by weight, and/or the amount of impurity D present in the high purity cangrelor is less than about 0.2% by weight, and/or the amount of impurity E present in the high purity cangrelor is less than about 0.5% by weight of the high purity cangrelor. In one aspect, the amount of impurities A and D present in the high purity cangrelor are each less than about 0.5% by weight of the high purity cangrelor.

In some aspects of this embodiment, the high purity cangrelor is stored in a chemically inert dry gas in a sealed vessel. When present, the chemically inert dry gas is nitrogen or argon.

In some aspects of this embodiment, the high purity cangrelor is stored in a stoppered, sealed dry vessel, wherein components thereof are sufficiently dried to minimize moisture transfer to cangrelor. In particular aspects, the stoppered, sealed dry vessel is a lyophilization vial stoppered with a stopper dried to minimize its own moisture level.

In a second embodiment, the invention relates to a pharmaceutical formulation comprising high purity cangrelor, or a salt thereof, as an active ingredient and one or more pharmaceutically acceptable excipients.

High purity cangrelor is cangrelor having a combined total of selected hydrolysis and oxidation degradants of cangrelor not exceeding about 1.5% by weight of the high purity cangrelor. Selected hydrolysis and oxidation degradants of cangrelor are impurity A, impurity B, impurity C, impurity D and impurity E. Thus, in one aspect of this embodiment, high purity cangrelor of the present invention has a combined impurity level of impurities A, B, C, D and E of less than about 1.5% by weight of the high purity cangrelor. In other aspects, high purity cangrelor of the present invention has a combined impurity level of impurities A, B, C, D and E of less than about 1.4% by weight, less than about 1.3% by weight, less than about 1.2% by weight or less than about 1.0% by weight. In another aspect, the amount of impurity A present in the high purity cangrelor is less than about 0.5% by weight, and/or the amount of impurity B present in the high purity cangrelor is less than about 0.2% by weight, and/or the amount of impurity C present in the high purity cangrelor is less than about 0.3% by weight, and/or the amount of impurity D present in the high purity cangrelor is less than about 0.2% by weight, and/or the amount of impurity E present in the high purity cangrelor is less than about 0.5% by weight of the high purity cangrelor. In one aspect, the amount of impurities A and D present in the high purity cangrelor are each less than about 0.5% by weight of the high purity cangrelor.

In certain aspects of this embodiment, the pharmaceutically acceptable excipient is a polyol. When present, the polyol is at least one member selected from the group consisting of mannitol and sorbitol. In one aspect, the invention relates to a pharmaceutical formulation consisting of high purity cangrelor, or a salt thereof, as an active ingredient and mannitol or sorbitol, or both mannitol and sorbitol.

In certain aspects of this embodiment, the pharmaceutical formulation comprises about 16-21% of high purity cangrelor, expressed in terms of the free acid but present as the free acid or a salt thereof, and about 84-79% of the one or more pharmaceutically acceptable excipients, by weight of the pharmaceutical formulation.

In some aspects of this embodiment, the pharmaceutical formulation is stored in a chemically inert dry gas in a sealed vessel. When present, the chemically inert dry gas is nitrogen or argon.

In some aspects of this embodiment, the pharmaceutical formulation is stored in a stoppered, sealed dry vessel, wherein components thereof are sufficiently dried to minimize moisture transfer to a component of the pharmaceutical formulation. In particular aspects, the stoppered, sealed dry vessel is a lyophilization vial stoppered with a stopper dried to minimize its own moisture level.

In a third embodiment, the invention relates to a method for preparing high purity cangrelor, or a salt thereof, comprising (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved, thereby preparing high purity cangrelor or a salt thereof. In one aspect, the invention relates to a method for preparing high purity cangrelor, or a salt thereof, consisting of (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved, thereby preparing high purity cangrelor or a salt thereof.

High purity cangrelor is cangrelor having a combined total of selected hydrolysis and oxidation degradants of cangrelor not exceeding about 1.5% by weight of the high purity cangrelor. Selected hydrolysis and oxidation degradants of cangrelor are impurity A, impurity B, impurity C, impurity D and impurity E. Thus, in one aspect of this embodiment, high purity cangrelor of the present invention has a combined impurity level of impurities A, B, C, D and E of less than about 1.5% by weight of the high purity cangrelor. In other aspects, high purity cangrelor of the present invention has a combined impurity level of impurities A, B, C, D and E of less than about 1.4% by weight, less than about 1.3% by weight, less than about 1.2% by weight or less than about 1.0% by weight. In another aspect, the amount of impurity A present in the high purity cangrelor is less than about 0.5% by weight, and/or the amount of impurity B present in the high purity cangrelor is less than about 0.2% by weight, and/or the amount of impurity C present in the high purity cangrelor is less than about 0.3% by weight, and/or the amount of impurity D present in the high purity cangrelor is less than about 0.2% by weight, and/or the amount of impurity E present in the high purity cangrelor is less than about 0.5% by weight of the high purity cangrelor. In one aspect, the amount of impurities A and D present in the high purity cangrelor are each less than about 0.5% by weight of the high purity cangrelor.

In some aspects of this embodiment, the pH of the second solution is about 7.0, about 7.5, about 8.0, about 8.5, about 9.0, about 9.5, between about 7.0 and 8.0, between about 7.5 and 8.5, between about 8.0 and 9.0, or between about 8.5 and 9.5.

In some aspects of this embodiment, mixing of (b) is achieved by adding the pH-adjusting agent to the first solution. In other aspects of this embodiment, the mixing of (b) is achieved by adding the first solution to the pH-adjusting agent. In further aspects of this embodiment, the mixing of (b) is achieved by simultaneous combination of the pH-adjusting agent and the first solution. In some of these aspects, the pH-adjusting agent is added to the first solution in portions. In other aspects, the pH-adjusting agent is added to the first solution at a constant rate. In some aspects of this embodiment, mixing is achieved by using one or more mixing devices. When used, the mixing device is selected from the group consisting of a paddle mixer, magnetic stirrer, shaker, re-circulating pump, homogenizer, and any combination thereof. Alternatively, the mixing device is a homogenizer, a bottom mount magnetic device, a paddle mixer, or a combination thereof. In further aspects of this embodiment, the mixing is achieved through high shear mixing.

In some aspects of this embodiment, removing the solvent (c) is through lyophilization.

In some aspects of this embodiment, one or more of the steps is performed in the absence of light, such as the mixing of (b).

In some aspects of this embodiment, one or more of the steps is performed under a chemically inert gas, in particular nitrogen, such as the mixing of (b).

In some aspects of this embodiment, the method further comprises sterilizing the second solution after the mixing of (b) and before the removal of the solvent. In one aspect, sterilization is achieved by aseptic filtration.

In some aspects of this embodiment, the method further comprises storing the high purity cangrelor or salt thereof in a chemically inert dry gas in a sealed vessel. When present, the chemically inert dry gas is nitrogen or argon.

In some aspects of this embodiment, the method further comprises storing the high purity cangrelor or salt thereof in a stoppered, sealed dry vessel, wherein components thereof are sufficiently dried to minimize moisture transfer to cangrelor. In particular aspects, the stoppered, sealed dry vessel is a lyophilization vial stoppered with a stopper dried to minimize its own moisture level.

In a fourth embodiment, the invention relates to a method for preparing a pharmaceutical formulation comprising high purity cangrelor, or a salt thereof, as an active ingredient and one or more pharmaceutically acceptable excipients, comprising (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved, wherein one or more pharmaceutically acceptable excipients is added to the first solution, or to the second solution, or to both, thereby preparing a pharmaceutical formulation comprising high purity cangrelor or a salt thereof.

High purity cangrelor is cangrelor having a combined total of selected hydrolysis and oxidation degradants of cangrelor not exceeding about 1.5% by weight of the high purity cangrelor. Selected hydrolysis and oxidation degradants of cangrelor are impurity A, impurity B, impurity C, impurity D and impurity E. Thus, in one aspect of this embodiment, high purity cangrelor of the present invention has a combined impurity level of impurities A, B, C, D and E of less than about 1.5% by weight of the high purity cangrelor. In other aspects, high purity cangrelor of the present invention has a combined impurity level of impurities A, B, C, D and E of less than about 1.4% by weight, less than about 1.3% by weight, less than about 1.2% by weight or less than about 1.0% by weight. In another aspect, the amount of impurity A present in the high purity cangrelor is less than about 0.5% by weight, and/or the amount of impurity B present in the high purity cangrelor is less than about 0.2% by weight, and/or the amount of impurity C present in the high purity cangrelor is less than about 0.3% by weight, and/or the amount of impurity D present in the high purity cangrelor is less than about 0.2% by weight, and/or the amount of impurity E present in the high purity cangrelor is less than about 0.5% by weight of the high purity cangrelor. In one aspect, the amount of impurities A and D present in the high purity cangrelor are each less than about 0.5% by weight of the high purity cangrelor.

In some aspects of this embodiment, the pH of the second solution is about 7.0, about 7.5, about 8.0, about 8.5, about 9.0, about 9.5, between about 7.0 and 8.0, between about 7.5 and 8.5, between about 8.0 and 9.0, or between about 8.5 and 9.5.

In some aspects of this embodiment, mixing of (b) is achieved by adding the pH-adjusting agent to the first solution. In other aspects of this embodiment, the mixing of (b) is achieved by adding the first solution to the pH-adjusting agent. In further aspects of this embodiment, the mixing of (b) is achieved by simultaneous combination of the pH-adjusting agent and the first solution. In some of these aspects, the pH-adjusting agent is added to the first solution in portions. In other aspects, the pH-adjusting agent is added to the first solution at a constant rate. In some aspects of this embodiment, mixing is achieved by using one or more mixing devices. When used, the mixing device is selected from the group consisting of a paddle mixer, magnetic stirrer, shaker, re-circulating pump, homogenizer, and any combination thereof. Alternatively, the mixing device is a homogenizer, a bottom mount magnetic device, a paddle mixer, or a combination thereof. In further aspects of this embodiment, the mixing is achieved through high shear mixing.

In certain aspects of this embodiment, the pharmaceutically acceptable excipient is a polyol. When present, the polyol is at least one member selected from the group consisting of mannitol and sorbitol. In one aspect, the one or more pharmaceutically acceptable excipient is mannitol or sorbitol, or both mannitol and sorbitol, and the excipient is added to the first solution. In another aspect, the one or more pharmaceutically acceptable excipient is mannitol or sorbitol, or both mannitol and sorbitol, and the excipient is added to the second solution. In one aspect, the invention relates to a method for preparing a pharmaceutical formulation consisting of high purity cangrelor, or a salt thereof, as an active ingredient and mannitol or sorbitol, or both mannitol and sorbitol, as a pharmaceutically acceptable excipient, comprising (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved, wherein the pharmaceutically acceptable excipient is added to the first solution, or to the second solution, or to both, thereby preparing a pharmaceutical formulation comprising high purity cangrelor or a salt thereof. In another aspect, the invention relates to a method for preparing a pharmaceutical formulation consisting of high purity cangrelor, or a salt thereof, as an active ingredient and mannitol or sorbitol, or both mannitol and sorbitol, as a pharmaceutically acceptable excipient, consisting of (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved, wherein the pharmaceutically acceptable excipient is added to the first solution, or to the second solution, or to both, thereby preparing a pharmaceutical formulation comprising high purity cangrelor or a salt thereof.

In certain aspects of this embodiment, the pharmaceutical formulation comprises about 16-21% of high purity cangrelor, expressed as the free acid but present as the free acid or a salt thereof, and about 84-79% of the one or more pharmaceutically acceptable excipients, by weight of the pharmaceutical formulation.

In some aspects of this embodiment, removing the solvent (c) is through lyophilization.

In some aspects of this embodiment, one or more of the steps is performed in the absence of light, such as the mixing of (b).

In some aspects of this embodiment, one or more of the steps is performed under a chemically inert gas, including nitrogen, such as the mixing of (b).

In some aspects of this embodiment, the method further comprises sterilizing the second solution after the mixing of (b) and before the removal of the solvent. In one aspect, sterilization is achieved by aseptic filtration.

In some aspects of this embodiment, the method further comprises storing the formulation in a chemically inert dry gas in a sealed vessel. When present, the chemically inert dry gas is nitrogen or argon.

In some aspects of this embodiment, the method further comprises storing the formulation in a stoppered, sealed dry vessel, wherein components thereof are sufficiently dried to minimize moisture transfer to a component of the pharmaceutical formulation. In particular aspects, the stoppered, sealed dry vessel is a lyophilization vial stoppered with a stopper dried to minimize its own moisture level.

In a fifth embodiment, the invention relates to high purity cangrelor, or a salt thereof, prepared by a method comprising (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved. In one aspect, the invention relates to high purity cangrelor, or a salt thereof, prepared by a method consisting of (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved.

High purity cangrelor is cangrelor having a combined total of selected hydrolysis and oxidation degradants of cangrelor not exceeding about 1.5% by weight of the high purity cangrelor. Selected hydrolysis and oxidation degradants of cangrelor are impurity A, impurity B, impurity C, impurity D and impurity E. Thus, in one aspect of this embodiment, high purity cangrelor of the present invention has a combined impurity level of impurities A, B, C, D and E of less than about 1.5% by weight of the high purity cangrelor. In other aspects, high purity cangrelor of the present invention has a combined impurity level of impurities A, B, C, D and E of less than about 1.4% by weight, less than about 1.3% by weight, less than about 1.2% by weight or less than about 1.0% by weight. In another aspect, the amount of impurity A present in the high purity cangrelor is less than about 0.5% by weight, and/or the amount of impurity B present in the high purity cangrelor is less than about 0.2% by weight, and/or the amount of impurity C present in the high purity cangrelor is less than about 0.3% by weight, and/or the amount of impurity D present in the high purity cangrelor is less than about 0.2% by weight, and/or the amount of impurity E present in the high purity cangrelor is less than about 0.5% by weight of the high purity cangrelor. In one aspect, the amount of impurities A and D present in the high purity cangrelor are each less than about 0.5% by weight of the high purity cangrelor.

In some aspects of this embodiment, the pH of the second solution is about 7.0, about 7.5, about 8.0, about 8.5, about 9.0, about 9.5, between about 7.0 and 8.0, between about 7.5 and 8.5, between about 8.0 and 9.0, or between about 8.5 and 9.5.

In some aspects of this embodiment, mixing of (b) is achieved by adding the pH-adjusting agent to the first solution. In other aspects of this embodiment, the mixing of (b) is achieved by adding the first solution to the pH-adjusting agent. In further aspects of this embodiment, the mixing of (b) is achieved by simultaneous combination of the pH-adjusting agent and the first solution. In some of these aspects, the pH-adjusting agent is added to the first solution in portions. In other aspects, the pH-adjusting agent is added to the first solution at a constant rate. In some aspects of this embodiment, mixing is achieved by using one or more mixing devices. When used, the mixing device is selected from the group consisting of a paddle mixer, magnetic stirrer, shaker, re-circulating pump, homogenizer, and any combination thereof. Alternatively, the mixing device is a homogenizer, a bottom mount magnetic device, a paddle mixer, or a combination thereof. In further aspects of this embodiment, the mixing is achieved through high shear mixing.

In some aspects of this embodiment, removing the solvent (c) is through lyophilization.

In some aspects of this embodiment, one or more of the steps is performed in the absence of light, such as the mixing of (b).

In some aspects of this embodiment, one or more of the steps is performed under nitrogen, such as the mixing of (b).

In some aspects of this embodiment, the method further comprises sterilizing the second solution after the mixing of (b) and before the removal of the solvent. In one aspect, sterilization is achieved by aseptic filtration.

In some aspects of this embodiment, the method further comprises storing the high purity cangrelor or salt thereof in a chemically inert dry gas in a sealed vessel. When present, the chemically inert dry gas is nitrogen or argon.

In some aspects of this embodiment, the method further comprises storing the high purity cangrelor or salt thereof in a stoppered, sealed dry vessel, wherein components thereof are sufficiently dried to minimize moisture transfer to cangrelor. In particular aspects, the stoppered, sealed dry vessel is a lyophilization vial stoppered with a stopper dried to minimize its own moisture level.

In a sixth embodiment, the invention relates to a pharmaceutical formulation comprising high purity cangrelor, or a salt thereof, as an active ingredient and one or more pharmaceutically acceptable excipients prepared by a method comprising (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved, wherein one or more pharmaceutically acceptable excipients is added to the first solution, or to the second solution, or to both.

High purity cangrelor is cangrelor having a combined total of selected hydrolysis and oxidation degradants of cangrelor not exceeding about 1.5% by weight of the high purity cangrelor. Selected hydrolysis and oxidation degradants of cangrelor are impurity A, impurity B, impurity C, impurity D and impurity E. Thus, in one aspect of this embodiment, high purity cangrelor of the present invention has a combined impurity level of impurities A, B, C, D and E of less than about 1.5% by weight of the high purity cangrelor. In other aspects, high purity cangrelor of the present invention has a combined impurity level of impurities A, B, C, D and E of less than about 1.4% by weight, less than about 1.3% by weight, less than about 1.2% by weight or less than about 1.0% by weight. In another aspect, the amount of impurity A present in the high purity cangrelor is less than about 0.5% by weight, and/or the amount of impurity B present in the high purity cangrelor is less than about 0.2% by weight, and/or the amount of impurity C present in the high purity cangrelor is less than about 0.3% by weight, and/or the amount of impurity D present in the high purity cangrelor is less than about 0.2% by weight, and/or the amount of impurity E present in the high purity cangrelor is less than about 0.5% by weight of the high purity cangrelor. In one aspect, the amount of impurities A and D present in the high purity cangrelor are each less than about 0.5% by weight of the high purity cangrelor.

In some aspects of this embodiment, the pH of the second solution is about 7.0, about 7.5, about 8.0, about 8.5, about 9.0, about 9.5, between about 7.0 and 8.0, between about 7.5 and 8.5, between about 8.0 and 9.0, or between about 8.5 and 9.5.

In some aspects of this embodiment, mixing of (b) is achieved by adding the pH-adjusting agent to the first solution. In other aspects of this embodiment, the mixing of (b) is achieved by adding the first solution to the pH-adjusting agent. In further aspects of this embodiment, the mixing of (b) is achieved by simultaneous combination of the pH-adjusting agent and the first solution. In some of these aspects, the pH-adjusting agent is added to the first solution in portions. In other aspects, the pH-adjusting agent is added to the first solution at a constant rate. In some aspects of this embodiment, mixing is achieved by using one or more mixing devices. When used, the mixing device is selected from the group consisting of a paddle mixer, magnetic stirrer, shaker, re-circulating pump, homogenizer, and any combination thereof. Alternatively, the mixing device is a homogenizer, a bottom mount magnetic device, a paddle mixer, or a combination thereof. In further aspects of this embodiment, the mixing is achieved through high shear mixing.

In certain aspects of this embodiment, the pharmaceutically acceptable excipient is a polyol. When present, the polyol is at least one member selected from the group consisting of mannitol and sorbitol. In one aspect, the one or more pharmaceutically acceptable excipient is mannitol or sorbitol, or both mannitol and sorbitol, and the excipient is added to the first solution. In another aspect, the one or more pharmaceutically acceptable excipient is mannitol or sorbitol, or both mannitol and sorbitol, and the excipient is added to the second solution. In one aspect, the invention relates to a pharmaceutical formulation consisting of high purity cangrelor, or a salt thereof, as an active ingredient and mannitol or sorbitol, or both mannitol and sorbitol, as a pharmaceutically acceptable excipient, prepared by a method comprising (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved, wherein the pharmaceutically acceptable excipient is added to the first solution, or to the second solution, or to both. In another aspect, the invention relates to a pharmaceutical formulation consisting of high purity cangrelor, or a salt thereof, as an active ingredient and mannitol or sorbitol, or both mannitol and sorbitol, prepared by a method consisting of (a) dissolving cangrelor or a salt thereof in a solvent to form a first solution; (b) mixing a pH-adjusting agent with the first solution to form a second solution, wherein the pH of the second solution is between about 7.0 and 9.5; and (c) removing the solvent from the second solution to produce high purity cangrelor or a salt thereof under conditions wherein a level of moisture of less than about 2.0% by weight is achieved, wherein the pharmaceutically acceptable excipient is added to the first solution, or to the second solution, or to both.

In certain aspects of this embodiment, the pharmaceutical formulation comprises about 16-21% of high purity cangrelor, expressed as the free acid but present as the free acid or a salt thereof, and about 84-79% of the one or more pharmaceutically acceptable excipients, by weight of the pharmaceutical formulation.

In some aspects of this embodiment, removing the solvent (c) is through lyophilization.

In some aspects of this embodiment, one or more of the steps is performed in the absence of light, such as the mixing of (b).

In some aspects of this embodiment, one or more of the steps is performed under nitrogen, such as the mixing of (b).

In some aspects of this embodiment, the method further comprises sterilizing the second solution after the mixing of (b) and before the removal of the solvent. In one aspect, sterilization is achieved by aseptic filtration.

In some aspects of this embodiment, the method further comprises storing the formulation in a chemically inert dry gas in a sealed vessel. When present, the chemically inert dry gas is nitrogen or argon.

In some aspects of this embodiment, the method further comprises storing the formulation in a stoppered, sealed dry vessel, wherein components thereof are sufficiently dried to minimize moisture transfer to a component of the pharmaceutical formulation. In particular aspects, the stoppered, sealed dry vessel is a lyophilization vial stoppered with a stopper dried to minimize its own moisture level.

In a seventh embodiment, the invention relates to a method of inhibiting platelet activation, aggregation, or both, comprising contacting platelets with an effective amount of a high purity cangrelor, or a salt thereof, thereby inhibiting platelet activation, aggregation, or both. The method is practiced in vitro, in vivo or ex vivo.

In an eighth embodiment, the invention relates to a method of inhibiting platelet granule release, comprising contacting platelets with an effective amount of a high purity cangrelor, or a salt thereof, thereby inhibiting platelet granule release. The method is practiced in vitro, in vivo or ex vivo.

In a ninth embodiment, the invention relates to a method of inhibiting platelet-leukocyte aggregation, comprising contacting platelets with an effective amount of a high purity cangrelor, or a salt thereof, thereby inhibiting platelet-leukocyte aggregation. The method is practiced in vitro, in vivo or ex vivo.

In a tenth embodiment, the invention relates to a method of inhibiting platelet-granulocyte aggregation, comprising contacting platelets with an effective amount of a high purity cangrelor, or a salt thereof, thereby inhibiting platelet-granulocyte aggregation. The method is practiced in vitro, in vivo or ex vivo.

In a eleventh embodiment, the invention relates to a method of inhibiting platelet loss from the blood, comprising contacting platelets with an effective amount of a high purity cangrelor, or a salt thereof, thereby inhibiting platelet loss from the blood. The method is practiced in vitro, in vivo or ex vivo.

In a twelfth embodiment, the invention relates to a method of inhibiting platelet activation, aggregation, or both, in a subject, comprising administering an effective amount of a pharmaceutical formulation of the present invention to a subject in need thereof, thereby inhibiting platelet activation, aggregation, or both, in a subject. In certain aspects, the subject may be undergoing percutaneous coronary intervention (PCI) or a catherization technique, or treatment for acute coronary syndromes (ACS) or a clotting disorder in general. In other aspects, the subject is undergoing an ECC-based medical procedure, a hypothermia-based medical procedure, or a hypothermic ECC-based medical procedure.

In a thirteenth embodiment, the invention relates to a method of inhibiting platelet granule release in a subject, comprising administering an effective amount of a pharmaceutical formulation of the present invention to a subject in need thereof, thereby inhibiting platelet granule release in a subject. In certain aspects, the subject may be undergoing percutaneous coronary intervention (PCI) or a catherization technique, or treatment for acute coronary syndromes (ACS) or a clotting disorder in general. In other aspects, the subject is undergoing an ECC-based medical procedure, a hypothermia-based medical procedure, or a hypothermic ECC-based medical procedure.

In a fourteenth embodiment, the invention relates to a method of inhibiting platelet-leukocyte aggregation in a subject, comprising administering an effective amount of a pharmaceutical formulation of the present invention to a subject in need thereof, thereby inhibiting platelet-leukocyte aggregation in a subject. In certain aspects, the subject may be undergoing percutaneous coronary intervention (PCI) or a catherization technique, or treatment for acute coronary syndromes (ACS) or a clotting disorder in general. In other aspects, the subject is undergoing an ECC-based medical procedure, a hypothermia-based medical procedure, or a hypothermic ECC-based medical procedure.

In a fifteenth embodiment, the invention relates to a method of inhibiting platelet-granulocyte aggregation in a subject, comprising administering an effective amount of a pharmaceutical formulation of the present invention to a subject in need thereof, thereby inhibiting platelet-granulocyte aggregation in a subject. In certain aspects, the subject may be undergoing percutaneous coronary intervention (PCI) or a catherization technique, or treatment for acute coronary syndromes (ACS) or a clotting disorder in general. In other aspects, the subject is undergoing an ECC-based medical procedure, a hypothermia-based medical procedure, or a hypothermic ECC-based medical procedure.

In a sixteenth embodiment, the invention relates to a method of inhibiting platelet loss from the blood of a subject, comprising administering an effective amount of a pharmaceutical formulation of the present invention to a subject in need thereof, thereby inhibiting platelet loss from the blood of a subject. In certain aspects, the subject may be undergoing percutaneous coronary intervention (PCI) or a catherization technique, or treatment for acute coronary syndromes (ACS) or a clotting disorder in general. In other aspects, the subject is undergoing an ECC-based medical procedure, a hypothermia-based medical procedure, or a hypothermic ECC-based medical procedure.

In a seventeenth embodiment, the invention relates to a method of treating or preventing stent thrombosis in a subject, comprising administering an effective amount of a pharmaceutical formulation of the present invention to a subject in need thereof, thereby treating or preventing stent thrombosis in a subject. In some aspects of the embodiment, a second anti-thrombotic agent is administered with the pharmaceutical formulation, sequentially or concurrently. In a particular aspect, the second anti-thrombotic agent is bivalirudin.

In an eighteenth embodiment, the invention relates to a method of reducing mortality in a subject undergoing stent implantation, comprising administering an effective amount of a pharmaceutical formulation of the present invention to a subject in need thereof, thereby reducing mortality in a subject undergoing stent implantation. In some aspects of the embodiment, a second anti-thrombotic agent is administered with the pharmaceutical formulation, sequentially or concurrently. In a particular aspect, the second anti-thrombotic agent is bivalirudin.

In a nineteenth embodiment, the invention relates to method of treating or preventing myocardial infarction in a subject, comprising administering an effective amount of a pharmaceutical formulation of the present invention to a subject in need thereof, thereby treating or preventing myocardial infarction in a subject. In some aspects of the embodiment, a second anti-thrombotic agent is administered with the pharmaceutical formulation, sequentially or concurrently. In a particular aspect, the second anti-thrombotic agent is bivalirudin.

In a twentieth embodiment, the invention relates to method of reducing mortality in a subject experiencing myocardial infarction, comprising administering an effective amount of a pharmaceutical formulation of the present invention to a subject in need thereof, thereby reducing mortality in a subject experiencing myocardial infarction. In some aspects of the embodiment, a second anti-thrombotic agent is administered with the pharmaceutical formulation, sequentially or concurrently. In a particular aspect, the second anti-thrombotic agent is bivalirudin.

In a twenty-first embodiment, the invention relates to a medicament comprising an effective amount of high purity cangrelor, or a salt thereof, and one or more pharmaceutically acceptable excipients useful for treating or preventing stent thrombosis, treating or preventing myocardial infarction, reducing mortality in a subject undergoing stent implantation, or reducing mortality in a subject experiencing myocardial infarction.

DETAILED DESCRIPTION

The present invention relates to (i) high purity cangrelor, or one or more salts thereof, (ii) pharmaceutical formulations comprising high purity cangrelor, or one or more salts thereof, as an active ingredient and one or more pharmaceutically acceptable excipients, (iii) methods for preparing such compounds and formulations, and (iv) methods for using high purity cangrelor and the pharmaceutical formulations in the inhibition of platelet activation and aggregation and methods of medical treatment of subjects.

Cangrelor (Formula I, also referred to as ARC69931MX) has the IUPAC chemical name [dichloro-[[[(2R,3S,4R,5R)-3,4-dihydroxy-5-[6-(2-methylsulfanylethylamino)-2-(3,3,3-trifluoropropylsulfanyl)purin-9-yl]oxolan-2-yl]methoxy-hydroxyphosphoryl]oxy-hydroxyphosphoryl]methyl] phosphonic acid and may also be referred to the mixed mono(anhydride) of N-[2-(methylthio)ethyl]-2-[(3,3,3-trifluoropropyl)thio]-5'-adenylic acid with dichloromethylenebisphosphonic acid. It is represented in its neutral form, but it is generally used in a pharmaceutical formulation as a salt, such as the tetrasodium salt. Other salts that may be used in pharmaceutical formulations include other alkali metal salts, e.g. lithium and potassium salts; ammonium salts; alkaline earth metal salts, e.g. calcium and magnesium salts and salts of the Group III elements, e.g. aluminum salts. Salts with suitable organic bases, for example, salts with hydroxylamine; lower alkylamines, e.g. methylamine or ethylamine; with substituted lower alkylamines, e.g. hydroxy substituted alkylamines; or with monocyclic nitrogen heterocyclic compounds, e.g. piperidine or morpholine; and salts with amino acids, e.g. with arginine, lysine etc, or an N-alkyl derivative thereof; or with an aminosugar, e.g. N-methyl-D-glucamine or glucosamine. Non-toxic, physiologically acceptable salts are preferred.

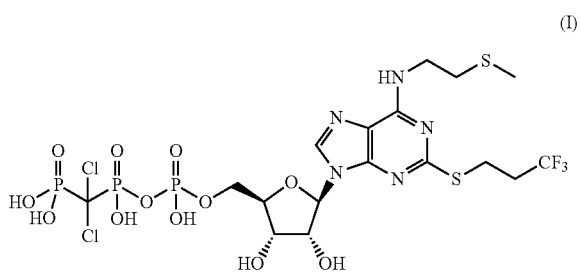 [SMILES: CSCCNc1nc(SCCC(F)(F)F)nc2c1ncn2[C@@H]1O[C@H](COP(=O)(O)OP(=O)(O)C(Cl)(Cl)P(=O)(O)O)[C@@H](O)[C@H]1O]

(I)

As used herein, reference to cangrelor should be understood to include both cangrelor in a neutral form, as well as one or more salts of cangrelor. Similarly, reference herein to high purity cangrelor should be understood to include both high purity cangrelor in a neutral form, as well as one or more salts of high purity cangrelor.

Methods for the synthesis of cangrelor are known in the art and described in, for example, U.S. Pat. No. 5,721,219 and U.S. Pat. No. 5,955,447, both of which are incorporated herein by reference in their entirety.

Cangrelor is a synthetic analogue of adenosine triphosphate (ATP) and a potent antagonist of the $P2Y_{12}$ receptor, a G-protein coupled purinergic receptor which is an important component of platelet activation (Dorsam, R. T.; Kunapuli, S. P. *J Clin Invest* 2003, 113, 340-345), with a $pIC_{50}$ of 9.35 (Chattaraj, S. C. *Curr Opin Investig Drugs* 2001, 2, 250-55; Diaz-Ricart, M. *Drugs Future* 2008, 33, 101-110). Inhibitors of platelet activation and aggregation are substances that are useful during percutaneous coronary intervention (PCI) and other catherization techniques in order to reduce bleeding complications, and in the treatment of acute coronary syndromes (ACS) and clotting disorders in general. The inhibition of platelet activation and aggregation, or antiplatelet therapy, has been recognized as a means to impact coagulation and inflammation in a way that conventional anticoagulant therapy is unable to (Bhatt, D. L.; Topol, E. J. *Nat Rev Drug Disc* 2003, 2, 15-28).

Cangrelor can be degraded to a number of impurities, including the following five impurities. Cangrelor can be degraded to dichloromethylenebisphosphonic acid (impurity E, Formula VI) and N-[2-(methylthio)ethyl]-2-[(3,3,3-trifluoropropyl)thio]-5'-adenylic acid (impurity A, Formula II) through the hydrolysis of the methylphosphonyl phosphate group (a mixed anhydride) or to (3,3,3-trifluoropropylthio)-N-(2-(methylthio)ethyl)-adenine (impurity D, Formula V) through the hydrolysis of the ribofuranoside. The first process is expected to be base catalyzed as is the hydrolysis of an anhydride and the second process is expected to be acid catalyzed as is the hydrolysis of a glycoside. Other degradants are also postulated to be generated through hydrolysis, such as N-[2-(methylthio)ethyl]-2-[(3,3,3-trifluoropropyl)thio]-5'-adenylic acid bis(anhydride) bonded to dichloromethylenebisphosphonic acid (impurity B, Formula III) which may form via the hydrolysis of cangrelor to impurity A followed by addition reaction with a second molecule of cangrelor. Other degradants result from non-hydrolytic processes, such as N-[2-(methylsulfinyl)ethyl]-2-[(3,3,3-trifluoropropyl)thio]-5'-adenylic acid monoanhydride bonded to dichloromethylenebisphosphonic acid (impurity C, Formula IV) which clearly occurs by oxidation of cangrelor. These degradants are found as impurities in cangrelor. Other impurities may be generated during the synthesis and the processing of cangrelor as well.

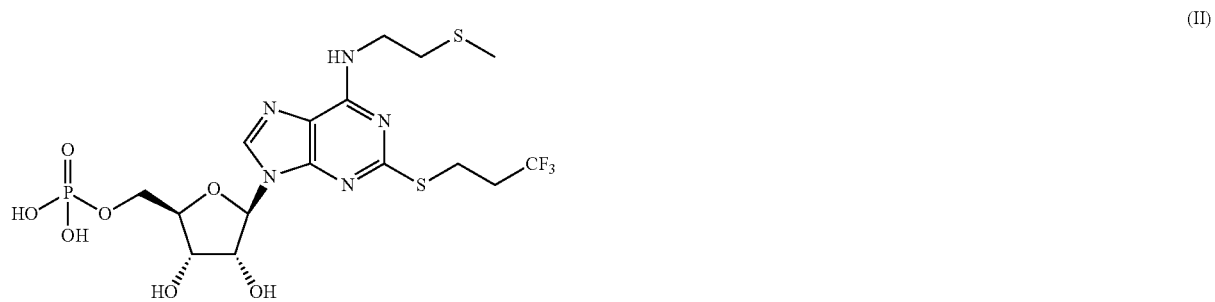

(II)

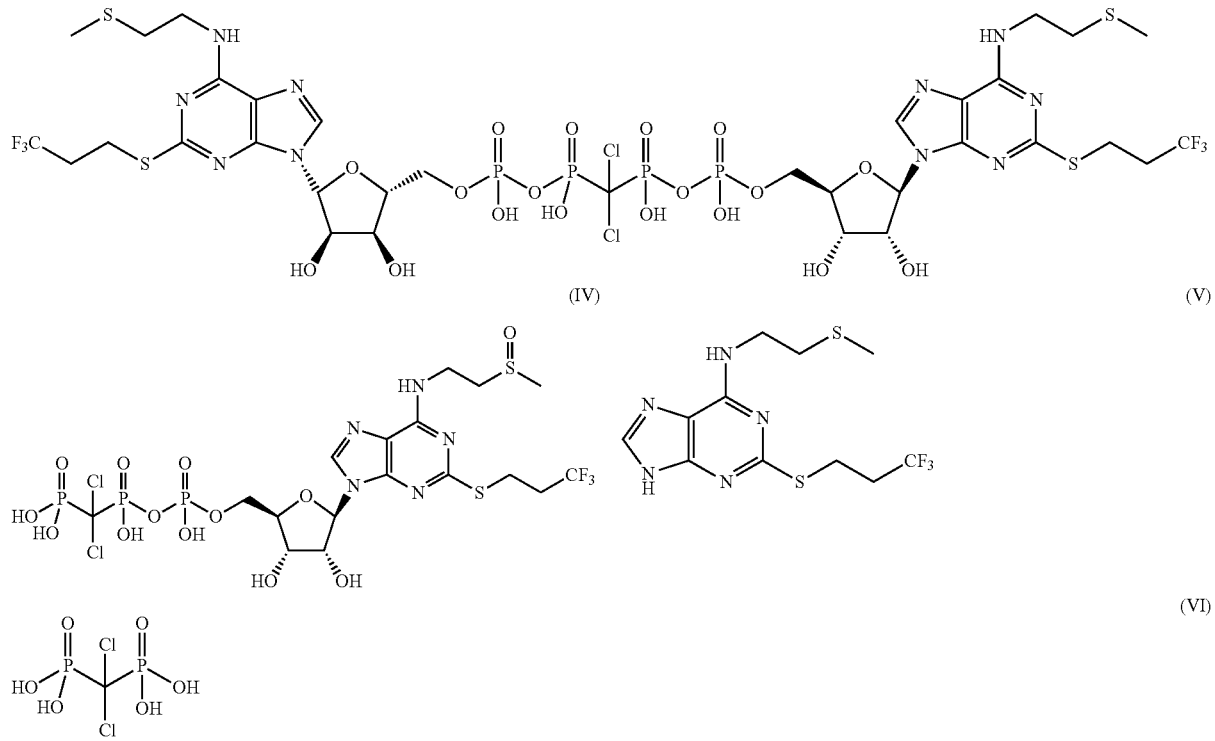

Those skilled in the art will also immediately recognize that impurities A, B, D and E are products of the hydrolysis of cangrelor whereas impurity C is the product of an oxidation of cangrelor. They will also recognize that the nature of cangrelor as an anhydride will result in some measure of reactivity towards water. These impurities will be generated from high purity cangrelor on handling and storage over time due to the presence of oxygen and water, present either as a solvent or as moisture. It is therefore critical that processes be put in place to manufacture pharmaceutical compositions of cangrelor with sufficiently high purity to be generated, stored and administered to patients.

The term "drug product" herein refers to an active ingredient of a pharmaceutical formulation. Thus, as used herein a drug product includes cangrelor, high purity cangrelor and all of the salts thereof.

Compounding Process for Preparing High Purity Cangrelor and Pharmaceutical Formulations Thereof High purity cangrelor, and salts thereof, and pharmaceutical formulations comprising the same are produced using a novel compounding process.

1) Dissolving Cangrelor in a Solvent to Form a Cangrelor Solution

In the compounding process of the present invention, cangrelor is dissolved in a solvent or a solvent mixture to form a cangrelor solution. Cangrelor may be commercially purchased or synthesized by various procedures as exemplified in U.S. Pat. No. 5,721,219 and U.S. Pat. No. 5,955,447. The concentration of cangrelor in the solvent may vary but it will generally be between about 0.5 mg/mL and about 100 mg/mL, preferably between about 1 mg/mL and about 50 mg/mL. In particular aspects, the concentration of cangrelor in the solvent is about 1 mg/mL, about 5 mg/mL, about 10 mg/mL, about 20 mg/mL, about 30 mg/mL, about 40 mg/mL, about 50 mg/mL, or about 60 mg/mL.

Solvents include aqueous and non-aqueous liquids, including but not limited to, mono- and di-alcohols such as methanol, ethanol, isopropyl alcohol, and propylene glycol; polyhydric alcohols such as glycerol and polyethylene glycol; buffers; and water. In a specific aspect, a 30 mg/mL solution of cangrelor in methanol is prepared. In another specific aspect, a 17 mg/mL solution of cangrelor in water is prepared.

Cangrelor can be dissolved in the solvent by methods known in the art, such as by adding cangrelor to the solvent. For example, cangrelor may be added to the solvent rapidly, slowly, in portions, at a constant rate, at a variable rate, or a combination thereof. A mixing device known in the art may be used to dissolve cangrelor. Examples of mixing devices include, but are not limited to, a paddle mixer, magnetic stirrer, shaker, re-circulating pump, bottom mount magnetic mixer, homogenizer, and any combination thereof. Suitable mixing rates will depend on such factors as the identity of the solvent, the desired final concentration, and the identity of the mixing device. However, suitable mixing rates include between about 50 and about 2000 rpm, such as between about 300 and about 1500 rpm. Dissolution may be performed at room temperature, at elevated temperature or at decreased temperature using techniques to control temperature known in the art. Preferably, the dissolution is performed at or below room temperature.

Dissolution may be performed by mixing cangrelor and the solvent in one portion or over smaller aliquots. Dissolution may also be performed over a selected period of time, for example, over 10 min to 1 h, including over 5 min to 10 min.

When pharmaceutical formulations are being prepared, one or more pharmaceutically acceptable excipients may be added to the solvent as well (also referred to herein as "acceptable excipient" and "excipient"). Excipients are components of a pharmaceutical formulation that serve to maintain, stabilize or alter the physico-chemical or physiological behavior of the active ingredient of a pharmaceutical formulation. Suitable excipients include, but are not limited to, agents that modify the lyophilization behavior of the active ingredient (e.g., cangrelor), agents that improve the rate of dissolution of the active ingredient, bulking agents and/or stabilizing agents. A bulking agent refers to any material that fills or provides volume to the active ingredient. A stabilizing agent refers to any material which serves to minimize degradation of the active ingredient. Examples of suitable excipients include, but are not limited to, polyols such as monosaccharides including glucose or fructose; a disaccharide including sucrose, maltose, or trehalose; an oligosaccharide; a polysaccharide; or a reduced sugar, such as sorbitol or mannitol. Exemplary excipients include mannitol, sorbitol, sucrose, lactose, fructose and trehalose, antioxidants, buffering agents, and preservatives. Preferred pharmaceutically acceptable excipients for cangrelor are exemplified, but not limited to, those described in U.S. Pat. No. 6,114,313 and U.S. Pat. No. 6,130,208.

The cangrelor solution and one or more excipients may be efficiently mixed using methods described above.

When present, the quantity of excipient will depend on factors such as the desired final concentration of cangrelor in the solvent, the identity of the solvent, and the means used to remove the solvent (as discussed below). However, in one aspect of the invention, the amount of excipient included in the cangrelor solution, when present, may be adjusted to provide a cangrelor solution having a ratio of the one or more excipients to the cangrelor of between about 5:1 and about 1:10 by weight, such as between about 3:1 and about 1:2, and about 1:2. In one aspect, two excipients are added to the solvent, for example two polyols, such as both sorbitol and mannitol.

The solution resulting from dissolving cangrelor in the solvent is referred to here as the "cangrelor solution" or alternatively the "first solution."

2) Preparing a pH-Adjusting Agent

The compounding process further comprises mixing a pH-adjusting agent with the cangrelor solution to form a compounding solution. The pH-adjusting agent may be prepared before, after, or simultaneously with the cangrelor solution.

The pH-adjusting agent may comprise a base dissolved or mixed in a solvent, or an acid dissolved or mixed in a solvent. When the pH-adjusting agent comprises a base, the base may be neat base such as a base which is liquid at room temperature, such as triethanolamine, a base which is solid at room temperature, such as sodium hydroxide, or a volatilizable base such as ammonium carbonate.

The base may be an organic base or an inorganic base. The terms "inorganic base" and "organic base", as used herein, refer to compounds that react with an acid to form a salt; compounds that produce hydroxide ions in an aqueous solution (Arrhenius bases); molecules or ions that capture hydrogen ions (Bronsted-Lowry bases); and/or molecules or ions that donate an electron pair to form a chemical bond (Lewis bases). In certain processes, the inorganic or organic base may be an alkali metal carbonate, an alkali metal bicarbonate, an alkaline earth metal carbonate, an alkali metal hydroxide, an alkaline earth metal hydroxide, an amine, or a phosphine. For example, the inorganic or organic base may be an alkali metal hydroxide such as sodium hydroxide, potassium hydroxide, cesium hydroxide, or lithium hydroxide; an alkali metal carbonate such as potassium carbonate or sodium carbonate; or an alkali metal bicarbonate such as sodium bicarbonate.

Solvents in which the base is dissolved or mixed may include aqueous and non-aqueous liquids, including but not limited to, mono- and di-alcohols such as methanol, ethanol, isopropyl alcohol, and propylene glycol; polyhydric alcohols such as glycerol and polyethylene glycol; buffers; and water. The pH-adjusting agent may also comprise one or more carriers such as dissolved polyols. For instance, the sugar may be a monosaccharide such as glucose or fructose; a disaccharide such as sucrose, maltose, or trehalose; an oligosaccharide; or a polysaccharide. The polyol may also be a reduced sugar, such as sorbitol or mannitol. There may be more than one carrier in the pH-adjusting agent. The quantity of the carrier in the pH-adjusting agent may be adjusted to provide the final product as described above.

The base is preferably mixed or dissolved in the solvent to form the pH-adjusting agent. The mixing or dissolution can be performed by methods known in the art. For instance, the base may be added to the solvent rapidly, slowly, in portions, at a constant rate, at a variable rate, or a combination thereof. Also, a mixing device known in the art may be used to mix the base and the solvent. Examples of mixing devices include, but are not limited to, a paddle mixer, magnetic stirrer, shaker, re-circulating pump, homogenizer, and any combination thereof. Suitable mixing rates will depend on such factors as the solvent, the desired final concentration, and the identity of the mixing device. However, suitable mixing rates may include between about 100 and about 1500 rpm, or between about 300 and about 1200 rpm. The base is added/mixed with the solvent in a quantity that will result in a pH-adjusting agent that is characterized as being between about 0.01 N and about 5 N, which includes between about 0.1 N and 1 N. The skilled artisan will understand that the specific normality of the pH-adjusting agent will vary depending on the characteristics of the cangrelor solution with which the pH-adjusting agent will be combined.

pH-adjusting agents are widely available and will be readily apparent to the skilled artisan. The following are non-limiting examples: acetic acid, ammonium carbonate, ammonium phosphate, boric acid, citric acid, lactic acid, phosphoric acid, potassium citrate, potassium metaphosphate, monobasic potassium phosphate, sodium acetate, sodium citrate, sodium lactate solution, dibasic sodium phosphate and monobasic sodium phosphate, sodium hydroxide, hydrochloric acid, sodium bicarbonate, sodium carbonate, potassium bicarbonate, potassium carbonate, potassium hydroxide, potassium phosphate, dibasic potassium phosphate, sodium phosphate and sodium borate.

3) Mixing the pH-Adjusting Agent with the Cangrelor Solution to Form a Compounding Solution The pH-adjusting agent may then be mixed with the cangrelor solution to form a compounding solution (also referred to herein as a "second solution"). This mixing may occur by adding the pH-adjusting agent to the cangrelor solution. Alternatively, the cangrelor solution may be added to the pH-adjusting agent, or the pH-adjusting agent and the cangrelor solution may be added simultaneously (into a separate vessel), or there may be a combination of these addition methods. It is important during the adding or mixing of the pH-adjusting agent and the cangrelor solution that pH is controlled. See below. Reference to the compounding solution can be a reference to the cangrelor solution during or after addition of the pH-adjusting agent, or it can be a reference to the pH-adjusting agent during or after addition of the cangrelor solution, or it can be a reference to the solution formed during or after combination of the pH-adjusting agent and the cangrelor solution.

The mixing of the pH-adjusting agent and the cangrelor solution may occur under controlled conditions. For example, temperature may be controlled by means known in the art, such as by mixing the pH-adjusting agent and the cangrelor solution in a vessel inside a cooling jacket. The temperature may be set between about 1° C. and about 25° C., including between about 2° C. and about 10° C. In some instances, the temperature may exceed 25° C. for limited periods of time. Also, the mixing of the pH-adjusting agent and the cangrelor solution may occur under additional controlled conditions, for example such as under an inert dry gas, such as nitrogen, and/or in the absence of light.

Levels of degradants due to hydrolysis in the compounding solution are minimized by achieving and maintaining a pH of between about 7.0 and about 9.5 in the compounding solution. Additional acceptable ranges include: between about 7.0 and about 8.0, between about 7.5 and about 8.5, between about 8.0 and about 9.0, between about 8.5 and about 9.5, between about 7.5 and about 9.5, between about 8.0 and about 9.5, between about 7.0 and about 9.0, and between about 7.0 and about 8.5. In particular aspects, the pH of the compounding solution is maintained at about pH 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, or 9.5.

While U.S. Pat. No. 6,114,313 teaches some limitations to the pH range in the final formulation of cangrelor, we have found that these limitations are insufficient to ensure the desired, low levels of degradants are reached. In addition, we have found that the pH range must be maintained throughout the process and not only in the final formulation.

While not wishing to be bound by theory, the degradants may also be generated by locally different pH or "hot spots," which are defined here as concentrated sites in the compounding solution that have much different pH levels than the surrounding environment. An example of a hot spot is a site in the compounding solution having a pH of about 12, while the surrounding solution has a pH of about 7. Degradation may also occur at such high pH levels in the compounding solution in general. It has been found that efficient and complete mixing reduces the generation of "hot spots" or high levels of pH in the compounding solution while the pH-adjusting agent and the cangrelor solution are being added or mixed. Thus, efficient mixing may control the overall pH level of the compounding solution to a level not exceeding about 10.5, or a level not exceeding about 10.0, or a level not exceeding about 9.5, or even a level not exceeding about 9.0.

Efficient mixing to minimize levels of degradation in the compounding solution may be achieved through various methods. One such method is to add or combine the pH-adjusting agent and the cangrelor solution portion-wise, i.e., in portions. For instance, the pH-adjusting agent may be added to the cangrelor solution in portions of set quantities, wherein each addition is separated by a period of time. The quantity of pH-adjusting agent may be approximately equal or may vary among the portions. For example, the pH-adjusting agent may be added in four portions, wherein each portion comprises about 25% of the total pH-adjusting agent quantity. As another example, the pH-adjusting agent may be added in three portions, such that the first portion comprises about 45% of the total pH-adjusting agent quantity, the second portion comprises about 30% of the total pH-adjusting agent quantity, and the third portion comprises about 25% of the total pH-adjusting agent quantity.

The pH-adjusting agent may also be added in portions such that there is a combination of equal and unequal quantities. For instance, the pH-adjusting agent may be divided into four portions, wherein the first portion comprises about 45% of the total pH-adjusting agent quantity, the second portion comprises about 25% of the total pH-adjusting agent quantity, and the third and fourth portions each comprise about 15% of the total pH-adjusting agent quantity.

The period of time between the additions of each portion may vary. This period may be a set duration of time regardless of the number of portions and/or volume of the portions to be added. Alternatively, the period of time may vary according to the number of portions and/or volume of the portions to be added. For example, the period of time between adding four equal portions may be about 5 minutes between each addition. As another example, the period of time after adding a first portion comprising about 60% of the total pH-adjusting agent quantity may be about 15 minutes, while the period of time after adding a second portion comprising about 40% of the total pH-adjusting agent quantity may be about 5 minutes.

The period of time between the additions of each portion may also be based upon a set total time for adding the pH-adjusting agent. For instance, if the total time for adding a pH-adjusting agent is set at about 20 minutes, then the period of time after adding each portion comprising about 25% of the total pH-adjusting agent quantity may be about 5 minutes. The period of time between the additions of each portion may also be based upon a set minimal time to allow for efficient mixing so as to avoid pH "hot spots". In certain embodiments of the present invention, the minimal time between the additions of two portions of the pH-adjusting agent may be a duration of between about 5 minutes and about 10 minutes, and in one example, between about 2 minutes and about 5 minutes, and in another example, between about 2 minutes and about 3 minutes.

Efficient mixing may also be achieved by adding the pH-adjusting agent to the cangrelor solution at a constant rate. The pH-adjusting agent may be added at a rate of between about 0.5% and about 50% of the total pH-adjusting agent quantity per minute; and in one example, between about 1% and about 25% of the total pH-adjusting agent quantity per minute; and in another example, between about 3% and about 8% of the total pH-adjusting agent quantity per minute.

The pH-adjusting agent may alternatively be added at a variable rate to the cangrelor solution. As an example, the rate may increase from about 5% to about 20% of the total pH-adjusting agent quantity per minute during the addition of the pH-adjusting agent.

The pH-adjusting agent may also be added to the cangrelor solution portion-wise, wherein each portion is added at a constant or variable rate. The portions may be added in equal amounts, unequal amounts, or a combination thereof. Further, each portion may be added at the same or different constant rates, or the same or different variable rates, or a combination thereof. As an example, the first portion comprising 60% of the total pH-adjusting agent may be added at 5% of the portion volume per minute, while four subsequent portions each comprising about 10% of the total pH-adjusting agent may be added at 10% of the portion volume per minute.

Furthermore, efficient mixing may be achieved through the use of one or more mixing devices. Examples of mixing devices include, but are not limited to, a paddle mixer, magnetic stirrer, shaker, re-circulating pump, homogenizer, and any combination thereof. The mixing rate of, for instance, a paddle mixer may be between about 100 rpm and 1000 rpm, and in one example, between about 400 rpm and about 800 rpm. The mixing rate for, as an example, a homogenizer (i.e., high shear mixing) may be between about 300 and about 6000 rpm, and in one example, between about 1500 rpm and about 3000 rpm.

The mixing device may mix continuously during the addition of the pH-adjusting agent, or at specific periods of time, e.g., between the additions of portions, after the pH-adjusting agent is added, etc.

In addition, more than one mixing device may be used when the pH-adjusting agent is added to the cangrelor solution. For example, a paddle mixer may be used at the surface of the cangrelor solution and a homogenizer may be used near the bottom of the cangrelor solution. When more than one mixing device is used, they may be operated at the same mixing rate or different mixing rates, or a combination thereof. The mixing devices may also be operated at the same periods of time, at different periods of time, or a combination thereof, during the addition of the pH-adjusting agent. Similarly, a mixing device may be used with the addition of the cangrelor solution to the pH-adjusting agent, or with the addition of the pH-adjusting agent and the cangrelor solution together.

Moreover, efficient mixing may be achieved through adding the pH-adjusting agent to specific sites within the cangrelor solution. For instance, the pH-adjusting agent may be added to the surface of the cangrelor solution or to the bottom of the cangrelor solution. In the cases wherein a mixing device is used, the pH-adjusting agent may be added to the site of the mixing device, e.g., at the site of the paddles of the paddle mixer or the blades of the homogenizer. The pH-adjusting agent may also be added to more than one site in the cangrelor solution; for example, the pH-adjusting agent may be added simultaneously at the top of the cangrelor solution and at the site of the mixing device. Alternatively, the cangrelor solution may be added to the pH-adjusting agent at specific sites and at more than one site within the pH-adjusting agent, as described above.

Optionally, once the compounding solution is formed, the pH or the final volume of the compounding solution may be adjusted to the target level before removal of the solvent (see below). The pH or volume can be adjusted using methods known in the art, for instance, the addition of additional solvent or pH-adjusting agent as described above.

When pharmaceutical formulations are being prepared, one or more pharmaceutically acceptable excipients may be added to the compounding solution. Such additions may be in place of the addition of excipients described above during production of a cangrelor solution, or in addition to the addition of excipients described above during production of a cangrelor solution. Thus, excipients can be added during production of the cangrelor solution, during production of the compounding solution, or both.

The timing and manner in which the excipients are added to the compounding solution is not critical. Thus, for example, the excipients may be added to the compounding solution before or after the pH-adjusting agent is added, or added during some or all of the period over which the pH-adjusting agent is added. Similarly, the compounding solution may be added to the excipient. Suitable excipients include an agent modifying the lyophilization behavior of the active pharmaceutical ingredient, an agent improving the rate of dissolution of the active pharmaceutical ingredient, a bulking agent or as a stabilizing agent. In some embodiments, the excipients may be polyols. For example, the polyol may be a monosaccharide such as glucose or fructose; a disaccharide such as sucrose, maltose, or trehalose; an oligosaccharide; or a polysaccharide. Alternatively, the polyol may be a reduced sugar, such as sorbitol or mannitol. The compounding solution and one or more excipients may be efficiently mixed using methods described above. The pH of the resulting solution may be checked and if it is found to be outside the desired range of between about pH 7.0 and about pH 9.5, additional pH-adjusting agent may be added to minimize generation of degradants.

When present, the quantity of excipient will depend on factors such as the desired final concentration of cangrelor in the compounding solution, the identity of the solvents, and the means used to remove the solvents (as discussed below). However, in one aspect of the invention, the compounding solution may be adjusted to provide a pharmaceutical formulation having a ratio of the one or more excipients to the cangrelor of between about 5:1 and about 1:10 by weight, such as between about 3:1 and about 1:2, and about 1:2. In one aspect, two excipients are added to the compounding solution, for example two polyols, such as both sorbitol and mannitol. Stated in another fashion, the pharmaceutical formulations of the invention comprise high purity cangrelor, expressed as the free acid but present as the free acid or a salt thereof, in a range of about 10-30% and one or more pharmaceutically acceptable excipients in a range of about 90-70%, by weight of the pharmaceutical formulation. In one aspect, the pharmaceutical formulations of the invention comprise high purity cangrelor, expressed as the free acid but present as the free acid or a salt thereof, in a range of about 15-25% and one or more pharmaceutically acceptable excipients in a range of about 85-75%, by weight. In another aspect, the pharmaceutical formulations of the invention comprise high purity cangrelor, expressed as the free acid but present as the free acid or a salt thereof, in a range of about 16-22% and one or more pharmaceutically acceptable excipients in a range of about 84-78%, by weight. In a further aspect, the pharmaceutical formulations of the invention comprise high purity cangrelor, expressed as the free acid but present as the free acid or a salt thereof, in a range of about 16-21% and one or more pharmaceutically acceptable excipients in a range of about 84-79%, by weight. In certain aspects, the amount of high purity cangrelor, expressed as the free acid, in a pharmaceutical formulation is not more than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1%, by weight of the formulation, with the remainder of the weight comprising the one or more pharmaceutically acceptable excipients, moisture and counterions.

When an excipient is added to the compounding solution, the pH or the volume of the solution may be determined after addition and, if needed, adjusted to the target level before removal of the solvent (see below). The pH or volume can be adjusted using methods known in the art, for instance, the addition of additional solvent or pH-adjusting agent as described above.

The compounding solution may also be sterilized before the removal of solvent. The compounding solution may undergo aseptic filtration using, for example, a membrane filter, such as 0.2 μm membrane filter, to sterilize the compounding solution. Techniques of sterilizing the compounding solution are known in the art (see, e.g., Berovic, M. *Biotechnol. Annu. Rev.* 2005, 11, 257-279, incorporated herein by reference in its entirety).

When the compounding solution is sterilized, the pH or the volume of the resulting solution may be determined after sterilization and, if needed, adjusted to the target level before removal of the solvent (see below). The pH or volume can be adjusted using methods known in the art, for instance, the addition of additional solvent or pH-adjusting agent as described above.

Furthermore, following sterilization, the compounding solution may be aliquoted into containers such as vials, bottles, ampoules, syringes, etc.

4) Removal of Solvent from the Compounding Solution

The compounding process further comprises removing solvents from the compounding solution.

Solvent removal from the compounding solution may be achieved through lyophilization, which comprises freezing the compounding solution and then reducing the surrounding pressure to allow the frozen solvent/moisture in the material to sublime directly from a solid phase to a gas phase. The lyophilization process may be performed by methods known in the art (see, e.g., Liu, J. *Pharm. Dev. Technol.* 2006, 11, 3-28; Tang, X.; Pikal, M. J. *Pharm. Res.* 2004, 21, 191-200; Nail, S. L.; Jiang, S.; Chongprasert, S.; Knopp, S. A. *Pharm. Biotechnol.* 2002, 14: 281-360; U.S. Pat. No. 7,351,431, and U.S. Pat. No. 6,821,515; each of which is incorporated herein by reference in its entirety).

Solvents may also be removed from the compounding solution through other techniques such as spray drying and spray-freeze drying (see, e.g., Lee, G. *Pharm. Biotechnol.* 2002, 13, 135-58; Maa, Y.-F.; Prestrelski, S. J. *Curr. Pharm. Biotechnol.* 2000, 1, 283-302; each of which is incorporated herein by reference in its entirety), vacuum drying, super critical fluid processing, air drying, or other forms of evaporative drying, as known in the art.

Lyophilization represents a process which generally comprises the steps of (a) chilling a solution to a temperature from about 5° C. to about −80° C., wherein the temperature is maintained for at least about 20 minutes to about 4 hours, (b) freezing the solution to a temperature of from about 0° C. to about −80° C., to produce a frozen mixture, wherein the temperature is maintained for at least about 30 minutes to about 20 hours, and (c) subjecting the frozen mixture to a primary drying stage, which comprises applying a vacuum to reduce the pressure by an amount effective to remove aqueous solvent from the frozen mixture, and, while applying the vacuum, changing the temperature of the frozen mixture to a primary drying temperature, wherein the primary drying temperature is from about 0° C. to about −50° C., and wherein the primary drying temperature is maintained for at least about 10 hours to about 50 hours.

Lyophilization may be performed over several steps, for example by conducting a step at a temperature range of between about −15° C. and about −50° C. and a pressure of between about 0.05 torr and about 0.5 torr and conducting a second step at a temperature range of between about −10° C. and about −20° C. and a pressure of between about 0.1 torr and about 0.5 torr. In other instances, only one lyophilization step may be required.

For example, the compounding solution may be frozen using such techniques as, but not limited to, mechanical refrigeration, dry ice, and liquid nitrogen. The temperature may be cooled to a range of between about 0° C. and about −80° C., and in one example, between about −10° C. and about −35° C. The primary lyophilization step may be characterized by a lowered pressure of between about 0.05 torr and about 10 torr, and in one example, between about 0.1 torr and about 1 torr. The secondary lyophilization step may be characterized by a pressure between about 0.05 torr and about 5 torr, and in one example, between about 0.1 torr and about 1 torr. In other instances, only one lyophilization step may be required.

In some instances, further drying may be performed after the bulk of the solvent was removed for example by maintaining the material at a temperature range of about 10° C. and 45° C. and a reduced pressure of between 0.05 torr and 5 torr, and in one example, at a temperature range of about 20° C. and 40° C. and a reduced pressure of between 0.1 torr and 1 torr. This additional drying step may be performed for a duration of between about 1 hour and about 10 hours, and in one example, between about 3 hours and about 6 hours In certain embodiments of the invention, removal of the solvent is effected under conditions where the residual moisture in the high purity cangrelor or salt thereof, and in a pharmaceutical formulation comprising high purity cangrelor, or a salt thereof, as an active ingredient, is less than about 2.0% on a weight basis to minimize the generation of degradants during further processing and storage. In other embodiments of the invention, the removal of the solvent will result in high purity cangrelor or salt thereof, and in a pharmaceutical formulation comprising high purity cangrelor, or a salt thereof, as an active ingredient, with less than about 2.0% moisture on a weight basis and a pH of between about 7.0 and about 9.5 to minimize the generation of degradants during further processing and storage. In aspects of these embodiments, the residual moisture is less than about 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2% or 0.1% on a weight basis.

The proper combinations of temperatures, reduced pressures and durations of the processes used for solvent removal are critical in order to minimize the levels of degradants generated during the processes, and upon storage of the high purity cangrelor or salt thereof and a pharmaceutical formulation comprising high purity cangrelor or a salt thereof.

A suitable process according to the invention is a vial freeze-drying process. Such a process comprises filling sterile vials with a sterile filtered solution of the composition according to the invention, such as a compounding solution. A sterile freeze-drying stopper is partially inserted into the vial which is frozen, e.g. at a temperature from −30 to −40° C., and thereafter vacuum dried in the frozen state. After drying, the stopper is fully inserted before removing the vial from the lyophilization unit.

It is possible that during solvent removal, the pH of the resulting material is altered, either as a result of the concentration of the base or as a result of the removal of a volatile base. The selected process must ensure that the pH of the compounding solution or of the resulting material remains in the range of about 7.0 to about 9.5.

The presence of degradants will increase over time as the compounding solution is stored or manipulated before the removal of solvent. Therefore the length of time between the dissolution of cangrelor to form the first solution and the removal of the solvent must be kept to a minimum to minimize the levels of the degradants generated. For example, this length of time should not exceed about 48 hours, and in aspects, not exceed about 36 hours, about 30 hours, about 24 hours, about 20 hours, about 16 hours, about 12 hours, about 8 hours, or about 4 hours.

To prevent oxidative processes brought about by the presence of oxygen and hydrolytic processes brought about by the presence of water, upon completion of the removal of the solvent, the resulting material obtained can be stored in an environment made of a chemically inert and moisture free gas within the storage vessel. This chemically inert and moisture free gas may be nitrogen or argon. In particular, the chemically inert dry gas can be introduced upon release of the vacuum at the end of lyophilization or vacuum drying cycles.

In aspects of the invention disclosed herein, the level of impurity A present in the high purity cangrelor or salt thereof, or in pharmaceutical formulations comprising the high purity cangrelor or salt thereof, is less than about 1.5, 1.4, 1.3, 1.2, 1.1, 1.0, 0.9, 0.8, 0.7, 0.6, 0.5, 0.4, 0.3, 0.2 or 0.1% by weight of the drug product.

In aspects of the invention disclosed herein, the level of impurity B present in the high purity cangrelor or salt thereof, or in pharmaceutical formulations comprising the high purity cangrelor or salt thereof, is less than about 1.0, 0.9, 0.8, 0.7, 0.6, 0.5, 0.4, 0.3, 0.2 or 0.1% by weight of the drug product.

In aspects of the invention disclosed herein, the level of impurity C present in the high purity cangrelor or salt thereof, or in pharmaceutical formulations comprising the high purity cangrelor or salt thereof, is less than about 1.0, 0.9, 0.8, 0.7, 0.6, 0.5, 0.4, 0.3, 0.2 or 0.1% by weight of the drug product.

In aspects of the invention disclosed herein, the level of impurity D present in the high purity cangrelor or salt thereof, or in pharmaceutical formulations comprising the high purity cangrelor or salt thereof, is less than about 1.0, 0.9, 0.8, 0.7, 0.6, 0.5, 0.4, 0.3, 0.2 or 0.1% by weight of the drug product.

In aspects of the invention disclosed herein, the level of impurity E present in the high purity cangrelor or salt thereof, or in pharmaceutical formulations comprising the high purity cangrelor or salt thereof, is less than about 1.0, 0.9, 0.8, 0.7, 0.6, 0.5, 0.4, 0.3, 0.2 or 0.1% by weight of the drug product.

In aspects of the invention disclosed herein, the combined level of impurities A and D present in the high purity cangrelor or salt thereof, or in pharmaceutical formulations comprising the high purity cangrelor or salt thereof, is less than about 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2 or 0.1% by weight of the drug product.

In aspects of the invention disclosed herein, the level of impurities A and D present in the high purity cangrelor or salt thereof, or in pharmaceutical formulations comprising the high purity cangrelor or salt thereof, is each less than about 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2 or 0.1% by weight of the drug product.

In aspects of the invention disclosed herein, the combined level of impurities A, B, C, D and E present in the high purity cangrelor or salt thereof, or in pharmaceutical formulations comprising the high purity cangrelor or salt thereof, is less than about 5.0, 4.5, 4.0, 3.5, 3.0, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2 or 0.1% by weight of the drug product. The particular impurities in the combined amount may vary in their individual concentrations or be about the same. Further, the skilled artisan will understand that any combination of the five impurities A, B, C, D and E, in any amount, may be present in the high purity cangrelor or salt thereof, although with a combined total of less than about 5.0% by weight of the drug product, and less than about 1.5% in some aspects. For example, there may be only one, or two, or three, or four, or all five of the impurities present in the high purity cangrelor or salt thereof.

5) Filling in Storage Vessels

The dried high purity cangrelor and pharmaceutical formulations comprising high purity cangrelor should be stored in a vessel that will prevent exposure of the drug product or formulations to moisture. In some aspects, exposure of the drug product or formulations to light may also be blocked. In a suitable example, the drug product and formulations are stored in sealed vessels such as stoppered vials. Filling of these vessels may be concomitant with solvent removal. That is, the compounding solution is loaded into the vessel and the solution is dried in the vessel as described above.

By methods known to those skilled in the art, vessels and their stoppers used for storing drug products and pharmaceutical formulations are washed, sterilized and dried prior to use. Residual moisture in vessels and their stoppers following this process can be transferred to the drug product and formulations over time and result in the appearance of degradants produced through hydrolytic process. Therefore, care should be taken to minimize the amount of residual moisture in the vessels and their stoppers.

The vessels must also be sealed sufficiently to ensure that oxygen and moisture do not penetrate over time, thereby minimizing the levels of degradants formed due to oxidative or hydrolytic processes. The vessels may be sealed by a stopper held in place by sleeves, by crimps or by overseals. The stoppers may be made from an elastic material such as rubber and the sleeves or crimps may be made from a malleable metal such as aluminum. The appropriateness of the seal can be checked by methods known to those skilled in the art, such as through helium leak detection (see, e.g., Kirsch, L. E.; Nguyen, L.; Moeckly, C. S. *PDA J Pharm Sci Technol.* 1997, 51,187-194, the disclosure of which is hereby incorporated by reference in its entirety). For example, the helium leak rate may be between about $1 \times 10^{-6}$ std.cc/sec and about $1 \times 10^{-4}$ std.cc/sec.

The components of the vessel, such as the stopper, that are made of elastic materials may be selected for their ability to absorb as little moisture as possible during washing and sterilization. These components may be made of butyl rubber.

Prior to use, the vessel and the stopper are dried at a sufficient temperature and for a sufficient duration to ensure that they transfer as little moisture as possible to the dried drug products and pharmaceutical formulations. For example, they may be dried at a temperature of about 70° C. to about 150° C. for a duration of about 1 hour to about 24 hours, such as about 1 hour to 4 hours.

In an embodiment of the invention, the sealed vessel and its components are selected and dried so that the amount of moisture found in the high purity cangrelor and pharmaceutical formulations comprising high purity cangrelor remains below 5.0% on a weight basis, and below 2.0% in some aspects, over a period of at least about 24 months. In particular aspects, the amount of moisture found in the high purity cangrelor and pharmaceutical formulations remains below 4.5, 4.0, 3.5, 3.0, 2.5, 2.4, 2.3, 2.2, 2.1, 2.0, 1.9, 1.8, 1.7, 1.6, 1.5, 1.4, 1.3, 1.2, 1.1, 1.0 or 0.5% on a weight basis over a period of at least about 3, 6, 9, 12, 15, 18, 21, 24, 36 or 48 months. The present invention also encompasses high purity cangrelor and pharmaceutical formulations defined in this manner.

In another embodiment of the invention, the sealed vessel and its components are selected and dried so that after a period of about 12 months, the high purity cangrelor and pharmaceutical formulations comprising high purity cangrelor are characterized by a pH of between about 7.0 and 9.5 for a 1% solution by weight, an amount of moisture less than about 5% on a weight basis (less than about 2.0% in some aspects), a maximum level of the impurities A, B, C and D not exceeding about 1% each by weight of the drug product (not exceeding 0.5% in some aspects) and a maximum level of impurity E not exceeding about 0.5% by weight of the drug product. The present invention also encompasses high purity cangrelor and pharmaceutical formulations defined in this manner.

In another embodiment of the invention, the sealed vessel and its components are selected and dried so that after a period of about 12 months, the high purity cangrelor and pharmaceutical formulations comprising high purity cangrelor are characterized by a pH of between about 7.0 and 9.5 for a 1% solution by weight, an amount of moisture less than about 5% on a weight basis (less than about 2.0% in some aspects), and a maximum level of impurity A not exceeding about 1% by weight of the drug product (not exceeding about 0.5% in some aspects), a maximum level of impurity B not exceeding about 0.5% by weight of the drug product (not exceeding about 0.2% in some aspects), a maximum level of impurity C not exceeding about 0.3% by weight of the drug product, a maximum level of impurity D not exceeding about 0.2% by weight of the drug product and a maximum level of impurity E not exceeding about 0.5% by weight of the drug product. The present invention also encompasses high purity cangrelor and pharmaceutical formulations defined in this manner.

In another embodiment of the invention, the sealed vessel and its components are selected and dried so that after a period of about 12 months, the high purity cangrelor and pharmaceutical formulations comprising high purity cangrelor are characterized by a pH of between about 7.0 and 9.5 for a 1% solution by weight, an amount of moisture less than about 5% on a weight basis (less than about 2.0% in some aspects), and a maximum combined level of impurities A, B, C, D and E not exceeding about 5.0% by weight of the drug product, or a maximum combined level of impurities A, B, C, D and E not exceeding about 2.0% by weight of the drug product, or a maximum combined level of impurities A, B, C, D and E not exceeding about 1.5% by weight of the drug product, or a maximum combined level of impurities A, B, C, D and E not exceeding about 1.3% by weight of the drug product. The present invention also encompasses high purity cangrelor and pharmaceutical formulations defined in this manner.

Formulations

The high purity cangrelor and pharmaceutical formulations of the present invention may be used in methods of inhibiting platelet activation and aggregation in vitro, in vivo and ex vivo. Such methods form the basis of therapeutic methods in animals such as humans. Providing high purity cangrelor and pharmaceutical formulations comprising high purity cangrelor in vessels, as discussed herein, will greatly aid in the practice of such methods.

The amount of high purity cangrelor or a pharmaceutical formulation comprising high purity cangrelor included in a vessel, such as a stoppered vial, will depend on the manner in which the drug product or formulation will be used. The amount may be one that allows the drug product or formulation to be reconstituted in the vessel and then used in vitro or ex vivo, or administered to a subject, without further dilution. Alternatively, the amount may be one that requires the drug product or formulation to be further diluted after reconstitution in the vessel and prior to use.

As an example, high purity cangrelor or a pharmaceutical formulation comprising the drug product may be supplied in single-use vials. Each single-use vial may contain about 50 mg of drug product or the formulation. When reconstituted with a sterile aqueous solution, a reconstituted solution with a pH of about 8-9.5 results. Reconstitution may be performed using water for injection, 0.9% NaCl, buffered saline, dextrose (e.g., 5% dextrose in water) or water as the sterile aqueous solution.

In some aspects, the pharmaceutical formulations of the present invention can be characterized by the amount of time required to reconstitute the formulations when mixed with a sterile aqueous solution. The reconstitution time, i.e., time required to put the pharmaceutical formulations in solution, may be characterized as not exceeding about 10, 9, 8, 7, 6, 5, 4, 3, 2, or 1 minute.

Reconstitution times may be determined, for example, by adding a selected level of sterile aqueous solution to a unit dosage vial comprising the cangrelor pharmaceutical formulation. Immediately after adding the appropriate solution (e.g., water, water for injection, saline, etc.), a timer is started. The vial is shaken vigorously, with inversion, for approximately 10 seconds. The vial is viewed to determine if the solid has dissolved. If the solid has not completely dissolved, the vial is shaken for another 10 seconds. These steps are repeated until all the solid dissolves, at which point the time is stopped and recorded.

When used in the treatment of a subject, the reconstituted formulation may be administered to a subject via parenteral modes of administration, including without limitation, intradermal, subcutaneous (s.c., s.q., sub-Q, Hypo), intramuscular (i.m.), intravenous (i.v.), intraperitoneal (i.p.), intra-arterial, intramedullary, intracardiac, intraspinal, and intrathecal (spinal fluids) modes. Any known device useful for parenteral injection or infusion of drug formulations can be used to effect such administration. In noted aspects and embodiments of the present invention, administration of the pharmaceutical compositions is via parenteral administration, preferably intravenous administration.

In intravenous (IV) administration, a sterile reconstituted formulation can be diluted in any of the commonly used intravenous fluids and administered by infusion. Intravenous fluids include, without limitation, physiological saline, 0.9% NaCl, phosphate buffered saline, 5% dextrose in water, 0.002% polysorbate 80 (Tween-80™) in water or Ringer's™ solution.

In intramuscular preparations, a sterile reconstituted formulation can be diluted and administered in a pharmaceutical diluent such as Water-for-Injection (WFI), physiological saline, 0.9% NaCl or 5% dextrose in water.

Suitable final concentrations of high purity cangrelor, or salt thereof, in the reconstituted formulations will vary depending on the particular use to which the formulation will be put, but may include high purity cangrelor, or salt thereof, at a concentration of about 0.1, 0.5, 1, 2, 3, 4, 5, 6, 7, 8, 9, or 10 mg/mL in 0.9% NaCl, or a concentration of about 0.1, 0.5, 1, 2, 3, 4, 5, 6, 7, 8, 9, or 10 mg/mL in 5% dextrose.

Dosage

As used herein, the terms "dose", "dosage", "unit dose", "unit dosage", "effective dose", "effective amount" and related terms refer to physically discrete units that contain a predetermined quantity of high purity cangrelor, or salt thereof, calculated to produce a desired therapeutic effect. These terms are synonymous with the therapeutically effective amounts and amounts sufficient to achieve the stated goals of the methods disclosed herein.

Particular doses of the pharmaceutical formulations of the present invention will vary depending upon the stated goals of the methods (treating, preventing or reducing), the physical characteristics of the subject, existence of related or unrelated medical conditions, the composition of the formulation and the means used to administer the drug product to the subject. The specific dose for a given subject will generally be set by the judgment of the attending physician.

When administered as an intravenous (IV) formulation, a pharmaceutical formulation comprising high purity cangrelor, or salt thereof, may be administered as a bolus, as a continuous infusion, or as a bolus followed by a continuous infusion. When administered as a bolus, a dose of about 5, 10, 15, 20, 25, 30, 35, 40, 45, 50, 55, 60, 65, 70, 75, 80, 85, 90, 95 or 100 µg/kg cangrelor, or more, is administered to the subject. In preferred embodiments, between about 20 and 40 µg/kg cangrelor is administered, more preferably about 30 µg/kg. When administered as a continuous infusion, cangrelor may be administered at about 0.1, 0.5, 0.75, 1, 2, 3, 4, 5, 6, 7, 8, 9, 10, 15, 20, 25, 30 µg/kg/min, or more, to the subject. In preferred embodiments, between about 0.1 and 10 µg/kg/min cangrelor is administered, more preferably about 4 µg/kg/min. The skilled artisan will understand that different dosages may be administered during different points of a medical procedure. Thus the dosages may differ in the periods before, during and after a medical procedure.

In each of the embodiments where the pharmaceutical formulation is administered as continuous intravenous infusion, the infusion may continue for at least about 10, 15, 20, 30, 40, 50, 60, 70, 80, 90, 100, 120, 130, 140, 150, 160, 170, 180, 190, 200, 220, 240, 260, 280, 300, 320, 340 or 360 minutes, or more. The skilled artisan will understand that the period of time over which the pharmaceutical formulation is administered may be shorter or longer than the indicated times due to the particular characteristics of a subject.

Where the pharmaceutical formulation is administered in conjunction with the implantation of a stent, such as during PCI, the bolus may be administered within about 360, 300, 240, 180, 120, 90, 60, 30 or 15 minutes prior to the beginning of the procedure.

In addition to the pharmaceutical formulations of the present invention comprising cangrelor, the skilled artisan will understand that one, two, three, four, five or more additional anti-thrombotic agents may be used in combination with cangrelor, such as bivalirudin. As a further example, aspirin (100-500 mg daily) may be administered in conjunction with the pharmaceutical formulations.

Using High Purity Cangrelor and Pharmaceutical Formulations

As indicated above, the high purity cangrelor and pharmaceutical formulations of the present invention may be used in methods of inhibiting platelet activation and aggregation in vitro, in vivo and ex vivo.

While not intending to be limited by doing so, the following are examples of particular methods that may be practiced using the high purity cangrelor or the pharmaceutical formulations of the present invention and are thus further embodiments of the invention.

In a general aspect, the present invention includes methods of inhibiting platelet activation, aggregation, or both, in a subject, comprising administering an effective amount of a pharmaceutical formulation of the present invention to a subject in need thereof, thereby inhibiting platelet activation, aggregation, or both, in a subject. The subject may be undergoing percutaneous coronary intervention (PCI) or another catherization technique. The subject may be undergoing treatment for acute coronary syndromes (ACS), or a clotting disorder in general.

In related embodiments, the present invention includes methods of inhibiting platelet granule release in a subject, comprising administering an effective amount of a pharmaceutical formulation of the present invention to a subject in need thereof, thereby inhibiting platelet granule release in a subject. The invention includes methods of inhibiting platelet-leukocyte aggregation in a subject, comprising administering an effective amount of a pharmaceutical formulation of the present invention to a subject in need thereof, thereby inhibiting platelet-leukocyte aggregation in a subject. The invention includes methods of inhibiting platelet-granulocyte aggregation in a subject, comprising administering an effective amount of a pharmaceutical formulation of the present invention to a subject in need thereof, thereby inhibiting platelet-granulocyte aggregation in a subject. The invention includes methods of inhibiting platelet loss from the blood of a subject, comprising administering an effective amount of a pharmaceutical formulation of the present invention to a subject in need thereof, thereby inhibiting platelet loss from the blood of a subject.

In a related aspect, the present invention includes methods of inhibiting platelet activation, aggregation, or both, comprising contacting platelets with an effective amount of a high purity cangrelor, or a salt thereof, thereby inhibiting platelet activation, aggregation, or both. The method may be practiced in vitro, in vivo or ex vivo.

In related embodiments, the present invention includes methods of inhibiting platelet granule release, comprising contacting platelets with an effective amount of a high purity cangrelor, or a salt thereof, thereby inhibiting platelet granule release. The invention includes methods of inhibiting platelet-leukocyte aggregation, comprising contacting platelets with an effective amount of a high purity cangrelor, or a salt thereof, thereby inhibiting platelet-leukocyte aggregation. The invention includes methods of inhibiting platelet-granulocyte aggregation, comprising contacting platelets with an effective amount of a high purity cangrelor, or a salt thereof, thereby inhibiting platelet-granulocyte aggregation. The invention includes methods of inhibiting platelet loss from the blood, comprising contacting platelets with an effective amount of a high purity cangrelor, or a salt thereof, thereby inhibiting platelet loss from the blood. The methods may be practiced in vitro, in vivo or ex vivo.

The pharmaceutical formulations of the present invention may be used in any disease, condition or procedure in a subject where platelet aggregation is involved. The pharmaceutical formulations of the present invention may thus act as anti-thrombotic agents and they are indicated in the treatment or prevention of diseases and conditions including, but not limited to, stent thrombosis, myocardial infarction, thromboembolic stroke and peripheral vascular disease. They are also indicated for use in reducing mortality in a subject undergoing stent thrombosis or experiencing myocardial infarction. They are further indicated in the treatment or prevention of the sequelae of thrombotic complications from angioplasty, stent implantation, thrombolysis, endarterectomy, coronary and vascular graft surgery, renal dialysis and cardio-pulmonary bypass. Additional indications include the treatment or prevention of disseminated intravascular coagulation, deep vein thrombosis, pre-eclampsia/eclampsia, tissue salvage following surgical or accidental trauma, vasculitis, arteritis, thrombocythaemia, ischemia and migraine.

The pharmaceutical formulations of the present invention are also indicated procedures such as percutaneous coronary intervention (PCI) and coronary artery bypass graft (CABG) surgery.

The present invention thus includes methods of protecting platelet function during medical procedures. Such medical procedures include one or more of extracorporeal circulation (ECC) and hypothermia. The methods comprise administering an effective amount of a pharmaceutical formulation of the present invention to a subject undergoing a medical procedure that includes ECC or hypothermia, or both. In embodiments of the methods, the invention is directed to methods of protecting platelets in the blood of a subject undergoing an ECC-based medical procedure, a hypothermia-based medical procedure or a hypothermic ECC-based medical procedure, where the method comprises administering an effective amount of a pharmaceutical formulation of the present invention to a subject undergoing such a procedure, thereby protecting platelets in the blood of the subject. The protection of platelets through these methods includes, but is not limited to, inhibiting activation of platelets, inhibiting platelet granule release, inhibiting platelet-leukocyte aggregation (including platelet-granulocyte aggregation), inhibiting platelet aggregation and inhibiting platelet loss from the blood of the subject.

Thus, in one embodiment the method inhibits activation of platelets in the blood of a subject undergoing an ECC-based medical procedure, a hypothermia-based medical procedure, or a hypothermic ECC-based medical procedure, wherein the method comprises administering an effective amount of a pharmaceutical formulation of the present invention to a subject undergoing such a procedure, thereby inhibiting activation of platelets in the blood of the subject.

A second embodiment the method inhibits platelet granule release in the blood of a subject undergoing an ECC-based medical procedure, a hypothermia-based medical procedure, or a hypothermic ECC-based medical procedure, and comprises administering an effective amount of a pharmaceutical formulation of the present invention to a subject undergoing such a procedure.

In a third embodiment the method inhibits platelet-leukocyte aggregation in the blood of a subject undergoing an ECC-based medical procedure, a hypothermia-based medical procedure, or a hypothermic ECC-based medical procedure, and comprises administering an effective amount of a pharmaceutical formulation of the present invention to a subject undergoing such a procedure. In one aspect, the platelet-leukocyte aggregation is platelet-granulocyte aggregation.

In a fourth embodiment the method inhibits platelet loss from the blood of a subject undergoing an ECC-based medical procedure, a hypothermia-based medical procedure, or a hypothermic ECC-based medical procedure, and comprises administering an effective amount of a pharmaceutical formulation of the present invention to a subject undergoing such a procedure.

The present invention includes methods of treating stent thrombosis. The course of treatment will generally follow implantation of a stent into a subject, where the subject is suspected of having or known to have developed a thrombus associated with a stent. The pharmaceutical formulation comprising cangrelor may be a bolus intravenous dosage form or a continuous intravenous infusion dosage form, and may be administered in combination with an oral dosage form. The course of treatment may last for a period of hours, days, weeks, months or years. The pharmaceutical formulation comprising cangrelor may thus be administered to a subject to treat stent thrombosis for about 1, 2, 3, 4, 5, 6, or 7 days, for about 1, 2, 3 or 4 weeks, or for about 1, 2, 3, 4, 5, 6, 7, 8, 9, 10, 11, 12 or more months, after the implantation of a vascular stent or after a diagnosis of stent thrombosis. In particular aspects, the pharmaceutical formulation may be administered to the subject as an intravenous bolus, as a continuous intravenous infusion, as an intravenous bolus followed by continuous intravenous infusion, or some combination thereof, and optionally, in combination with an oral dosage form. In a particular example, the pharmaceutical formulation is administered to the subject in a continuous intravenous infusion dosage form over a period of at least about 0.5, 1, 1.5, 2, 2.5, 3, 3.5 or 4 hours, or more. The methods of treatment of the present invention include methods wherein the pharmaceutical formulation is administered to the subject beginning about 1, 2, 3, 4, 5, 6, 7, 8, 9, 10, 11, 12, 13, 14 or 15 months, or more, after stent implantation. The treatment may be once, twice, thrice or more times a day, once every two days, once every three days, once every four days, once every five days, once every six days, once a week, once every 10 days, once every two weeks, once every three weeks, once a month, or even less frequently.

The present invention includes methods of preventing stent thrombosis or reducing mortality in a subject undergoing stent implantation. The course of prevention will generally be associated with a medical procedure in which a stent is being implanted into the subject. The course of treatment may be limited to the administration of the pharmaceutical formulation prior to the beginning of the procedure, during the procedure or after the procedure. Alternatively, the course of treatment may comprise administering the pharmaceutical formulation prior to the procedure and during the procedure, or during the procedure and after the procedure, or prior to the procedure and after the procedure. The skilled artisan will also understand that the course of treatment may begin prior to the procedure and continue until some point after the completion of the procedure. The skilled artisan will understand that the pharmaceutical formulation may be administered to the subject via different dosage forms, such as via intravenous infusion during the procedure and an oral dosage form for a number of days or months after the procedure has been completed.

When administered before stent implantation, the pharmaceutical formulation is preferably administered to the subject in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to stent implantation. When administered as a continuous intravenous infusion dosage form, the pharmaceutical composition is preferably administered to the subject as a continuous intravenous infusion over about a 0.5, 1, 1.5, 2, 2.5, 3, 3.5 or 4 hour period, or more.

When administered during stent implantation, the pharmaceutical formulation is preferably administered to the subject in an oral dosage form, a bolus intravenous dosage form, a continuous intravenous infusion dosage form, or as an intravenous bolus followed continuous intravenous infusion. When administered as a continuous intravenous infusion, the infusion may continue over about a 0.5, 1, 1.5, 2, 2.5, 3, 3.5 or 4 hour period, or more. The continuous intravenous infusion may also simply last for the duration of the procedure.

When administered after stent implantation, the pharmaceutical formulation is preferably administered to the subject in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

When administered both before and during the procedure, the pharmaceutical formulation may be administered to the subject in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to stent implantation, and administered to the subject in an oral dosage form, a bolus intravenous dosage form, a continuous intravenous infusion dosage form, or as an intravenous bolus followed continuous intravenous infusion, during the procedure. When administered as a continuous intravenous infusion, the infusion may continue over about a 0.5, 1, 1.5, 2, 2.5, 3, 3.5 or 4 hour period, or more. The continuous intravenous infusion may also simply last for the duration of the procedure.

When administered during and after the procedure, the pharmaceutical formulation may be administered to the subject in an oral dosage form, a bolus intravenous dosage form, a continuous intravenous infusion dosage form, or as an intravenous bolus followed continuous intravenous infusion, and administered to the subject in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

When administered both before and after the procedure, the pharmaceutical formulation may be administered to the subject in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to stent implantation, and administered to the subject in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

When administered before, during and after the procedure, the pharmaceutical formulation may be administered to the subject (i) in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to the procedure, (ii) in an oral dosage form, a bolus intravenous dosage form, a continuous intravenous infusion dosage form, or as an intravenous bolus followed continuous intravenous infusion, during the procedure, and (iii) in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When the dosage form is continuous intravenous infusion, the infusion may continue over about a 0.5, 1, 1.5, 2, 2.5, 3, 3.5 or 4 hour period, or more.

In the methods of the invention directed to methods of reducing mortality in a subject undergoing stent implantation, mortality may be reduced within a period of about 24, 36 or 48 hours after stent implantation, within a period of about 30 days after stent implantation, within a period of about six months after stent implantation, or within a period of about one year after stent implantation. In preferred embodiments, mortality is reduced by at least about 0.2%, 0.4%, 0.6%, 0.8%, 1.0% or 1.2% during the period in comparison to a subject not receiving cangrelor.

Stent thrombosis may result from any means related to the implantation, presence, or maintenance of a stent in the vasculature of a subject. For example, stent thrombosis may be induced by implantation of a stent, such as bare-metal stent or a drug-eluting stent, into a subject. Similarly, stent thrombosis may develop over time due to the presence of a stent, such as a bare-metal stent or a drug-eluting stent, in the subject. Thus, in each of these methods, stent thrombosis may be intraprocedural stent thrombosis, acute stent thrombosis, sub-acute stent thrombosis, late stent thrombosis or very late stent thrombosis. Further, in each of these methods, the prevention of stent thrombosis may be prevention during percutaneous coronary intervention (PCI) or other vascular stent implantation.

In each of the relevant methods, mortality may be caused by intraprocedural stent thrombosis, acute stent thrombosis, sub-acute stent thrombosis, late stent thrombosis or very late stent thrombosis, or occlusion of a coronary artery.

Stent thrombosis may result from any means related to the implantation, presence, or maintenance of the stent in the vasculature of a subject. For example, stent thrombosis may be induced by implantation of a stent, such as a bare-metal stent, a drug-eluting stent, or other type of stent into the subject. Similarly, stent thrombosis may develop over time due to the presence of a stent, such as a bare-metal stent, a drug-eluting stent, or other type of stent in the subject. Thus, in each of the embodiments of the present invention stent thrombosis may be intraprocedural stent thrombosis, acute stent thrombosis (<24 hours post implantation), sub-acute stent thrombosis (>24 hours and <30 days post implantation), late stent thrombosis (>30 days and <12 months post implantation) or very late stent thrombosis (>12 months post implantation).

In each of the relevant methods, the prevention of stent thrombosis may be prevention in the course of stent implantation during percutaneous coronary intervention (PCI) or other vascular stent implantation procedure.

In each of the relevant methods, the stent implantation may be implantation of a bare-metal stent, a drug-eluting stent, or other type of stent into a subject. The stent implantation is implantation during percutaneous coronary intervention (PCI) or other vascular stent implantation. The mortality associated with stent implantation may be mortality due to intraprocedural stent thrombosis, acute stent thrombosis, sub-acute stent thrombosis, late stent thrombosis or very late stent thrombosis.

The present invention includes a method of treating myocardial infarction or reducing mortality in a subject experiencing myocardial infarction. The course of treatment will generally follow diagnosis of myocardial infarction or at the onset of symptoms of myocardial infarction. The pharmaceutical formulation may be a bolus intravenous dosage form or a continuous intravenous infusion dosage form, and may be administered in combination with an oral dosage form. In preferred aspects, the pharmaceutical formulation is administered to the subject within about 5, 10, 15, 20, 30, 40, 50, 60, 70, 80 or 90 minutes of the onset of symptoms of myocardial infarction. The course of treatment may last for a period of hours, days or weeks. The pharmaceutical formulation may thus be administered to a subject to treat myocardial infarction or to reduce mortality for about 1, 2, 3, 4, 5 or more hours after diagnosis of myocardial infarction or at the onset of symptoms of myocardial infarction, and be repeated for a number of days or weeks. In particular aspects, the pharmaceutical formulation may be administered to the subject as an intravenous bolus, as a continuous intravenous infusion, as an intravenous bolus followed by continuous intravenous infusion, or some combination thereof, and optionally, in combination with an oral dosage form. In a particular example, the pharmaceutical formulation is administered to the subject in a continuous intravenous infusion dosage form over a period of at least about 0.5, 1, 1.5, 2, 2.5, 3, 3.5 or 4 hours, or more. The treatment may be once, twice, thrice or more times a day, once every two days, once every three days, once every four days, once every five days, once every six days, once a week, once every 10 days, once every two weeks, once every three weeks, once a month, or even less frequently.

In the methods of the invention directed to methods of reducing mortality in a subject experiencing myocardial infarction, mortality may be reduced within a period of about 24, 36 or 48 hours after myocardial infarction, within a period of about 30 days after myocardial infarction, within a period of about six months after myocardial infarction, or within a period of about one year after myocardial infarction. In preferred embodiments, mortality is reduced by at least about 0.2%, 0.4%, 0.6%, 0.8%, 1.0% or 1.2% during the period in comparison to a subject not receiving cangrelor.

The present invention includes a method of preventing myocardial infarction. The method comprises administration of a pharmaceutical formulation of the present invention to a subject as a prophylaxis against myocardial infarction. Subjects appropriate for such prevention would be any subject suspected of having a vascular thrombus, early symptoms of myocardial infarction or other disease or condition that could lead to myocardial infarction against which the pharmaceutical formulations of the invention would be effective. The pharmaceutical formulation may be in an oral dosage form, a bolus intravenous dosage form or a continuous intravenous infusion dosage form. In preferred aspects, the pharmaceutical formulation is administered to the subject within about 5, 10, 15, 20, 30, 40, 50, 60, 70, 80 or 90 minutes of when early or initial symptoms of myocardial infarction are detected. The course of treatment may last for a period of hours, days or weeks. The pharmaceutical formulation may thus be administered to a subject to prevent myocardial infarction for about 1, 2, 3, 4, 5 or more hours after early or initial symptoms of myocardial infarction are detected, and be repeated for a number of days or weeks. In particular aspects, the pharmaceutical formulation may be administered to the subject orally, as an intravenous bolus, as a continuous intravenous infusion, as an intravenous bolus followed by continuous intravenous infusion, or some combination thereof. In a particular example, the pharmaceutical formulation is administered to the subject in a continuous intravenous infusion dosage form over a period of at least about 0.5, 1, 1.5, 2, 2.5, 3, 3.5 or 4 hours, or more. The treatment may be once, twice, thrice or more times a day, once every two days, once every three days, once every four days, once every five days, once every six days, once a week, once every 10 days, once every two weeks, once every three weeks, once a month, or even less frequently.

In each of the relevant methods, myocardial infarction may be any form of myocardial infarction, including acute myocardial infarction (first few hours to 7 days), healing myocardial infarction (7 to 28 days), healed myocardial infarction (29 days and beyond), acute non-ST-elevated myocardial infarction and acute ST-elevated myocardial infarction. Myocardial infarction may be induced by any mechanism, including implantation of a bare-metal stent or a drug-eluting stent into the subject, or other vascular stent implantation, or arise during percutaneous coronary intervention (PCI). Myocardial infarction may also be caused by intraprocedural stent thrombosis, acute stent thrombosis, sub-acute stent thrombosis, late stent thrombosis, very late stent thrombosis or occlusion of a coronary artery. Mortality may be caused by intraprocedural stent thrombosis, acute stent thrombosis, sub-acute stent thrombosis, late stent thrombosis or very late stent thrombosis, or occlusion of a coronary artery.

Subjects

As used herein, a "subject" upon which the methods of the present invention may be practiced refers to an animal, such as a mammalian or an avian species, including a human, a non-human primate, a horse, a cow, a sheep, a goat, a dog, and a cat.

To further characterize the subjects to which the methods of the present invention may be applied, it is noted that the subject may have suffered a stroke, or the subject may not have suffered a stroke. The subject may have diabetes mellitus, or the subject may not have diabetes mellitus. The subject may have hypertension, or the subject may not have hypertension. The subject may have hyperlipidemia, or the subject may not have hyperlipidemia. The subject may have suffered a myocardial infarction, or the subject may not have suffered a myocardial infarction. The subject may have a family history of coronary artery disease (CAD), or the subject may not have a family history of CAD. The subject may have undergone percutaneous transluminal coronary angioplasty (PTCA), or the subject may not have undergone PTCA. The subject may have undergone percutaneous coronary intervention (PCI), or the subject may not have undergone PCI. The subject may have undergone coronary artery bypass graft (CABG), or the subject may not have undergone CABG. The subject may have congestive heart failure, or the subject may not have congestive heart failure. The subject may have peripheral arterial disease (PAD), or the subject may not have PAD.

In certain aspects, the subject may have stent thrombosis, be at risk of developing stent thrombosis, or be undergoing stent implantation. The subject may have stent thrombosis in more than one artery or vein. Thus, the subjects encompassed by the methods of the present invention include subjects undergoing vascular stent implantation and subjects having undergone vascular stent implantation.

In certain aspects, the subject may be undergoing coronary artery bypass grafting (CABG) surgery or about to undergo CABG surgery (e.g., in less than 10, 9, 8, 7, 6, 5, 4, 3, 2 or 1 day). Such subjects may have an acute coronary syndrome (ACS) and/or have been treated with a coronary stent. Such patients may also have been receiving thienopyridine treatment prior to treatment using one of the methods of the present invention. For example, the subject may be treated using a method of the present invention as a "bridge" between cessation of oral antiplatelet therapy and the beginning of cardiac surgery.

Results of the Methods

Each of the methods recited in the present invention may include the additional step of measuring the effect or effectiveness of the pharmaceutical formulation during or after administration. In one example, the additional step of measuring an effect of the pharmaceutical formulation may be performed during or about 0.5, 1, 1.5, 2, 2.5, 3, 3.5, 4, 4.5, 5, 10, 15, 20 or 24 hours, or more, after completion of a method of the invention. The effects that may be measured in the methods of the present invention include a change in the level of platelet reactivity, an increase in luminal diameter within the stent, a decrease in the size of the stent thrombus, and a decreased incidence of myocardial infarction. Each of these effects would demonstrate the effectiveness of the compounds comprising the pharmaceutical composition.

The invention will now be further described by way of the following non-limiting examples, which further illustrate the invention, and are not intended, nor should they be interpreted to, limit the scope of the invention.

EXAMPLES

Example 1

Solution Stability of Cangrelor Tetrasodium

Given the nature of cangrelor as an anhydride, its stability in aqueous solution was determined.

Solutions of cangrelor in water at 1 mg/mL were stored at 4° C., 25° C. and 40° C. for 8 days and protected from light. The levels of the impurities were determined by reverse phase HPLC and reported in Table 1.

TABLE 1

Solution stability of Cangrelor (1 mg/mL) in purified water for 8 days

| | | Measured level (% w/w) | | |
| | | After 8 days under storage conditions described | | |
| Measured analyte | Initial | 4° C. and ambient humidity | 25° C. and 60% relative humidity | 40° C. and ambient humidity |
| Cangrelor | 98.23 | 98.45 | 96.94 | 90.46 |
| Impurity A | 0.16 | 0.22 | 1.58 | 7.50 |
| Impurity D | ND | ND | ND | ND |
| Impurity C | 0.28 | 0.26 | 0.27 | 0.37 |
| Total Impurities* | 1.76 | 1.54 | 3.06 | 9.56 |

ND - none detected.
*includes all impurities including those formed during the synthesis of cangrelor.

The results demonstrate that cangrelor is a moisture-sensitive molecule, in particular through hydrolysis to impurity A. Therefore, it is important to control the moisture content of the solid cangrelor.

Example 2

Accelerated pH Stability of High Purity Cangrelor

The stability of cangrelor drug substance in aqueous solution was investigated over a range of pH values. The extent of degradation was determined using a reverse phase HPLC method. The effect of pH on the stability of cangrelor in aqueous solution at 1 mg/mL was studied over a pH range of 1 to 12 and the solutions were stored at 40° C. for 7 days protected from light (Table 2).

TABLE 2

Stability of Cangrelor in various pH buffer solutions for 7 days at 40° C. protected from light

| pH | Medium | Impurity A (% w/w) | Impurity D (% w/w) | Total Impurities* (% w/w) |
| --- | --- | --- | --- | --- |
| 1.0 | 0.1M HCl | 28.51 | 68.12 | 97.28 |
| 3.0 | Phosphate | 28.69 | 0.81 | 31.48 |
| 5.0 | Phosphate | 20.70 | ND | 22.16 |
| 7.0 | Phosphate | 14.31 | ND | 15.71 |
| 9.0 | Phosphate | 3.25 | ND | 4.90 |
| 11.0 | Phosphate | 2.61 | ND | 4.28 |
| 12.0 | 0.1M NaOH | 2.42 | ND | 4.39 |

ND - none detected.
*Sum of all impurities including degradants and impurities occurring during the synthesis of cangrelor.

The degradation of cangrelor after 7 days at 40° C. was pH dependent and occurred primarily via hydrolysis of cangrelor to form either impurity A (hydrolysis of the dichloromethylenebisphosphonic acid group on cangrelor) or impurity D (hydrolysis of the glycosidic bond on cangrelor) or both impurity A and impurity D. Based on the pH stability data, it is evident that cangrelor is more sensitive to hydrolysis in acidic pH but progressively more stable in the alkaline pH range. The main route of degradation at lower pH (1-3) is the hydrolysis of the glycosidic bond to form impurity D, which is expected on the basis of the lability of glycosidic bonds to acid hydrolysis. This particular degradation pathway was not detected at pH 5 or higher. On the other hand, there is a reduction in the rate of the hydrolysis pathway leading to impurity A with increasing pH.

While these conditions (40° C. for 7 days) are not representative of storage conditions for the pharmaceutical formulation comprising cangrelor, they provide for a convenient way to evaluate the impact of pH on the degradation of cangrelor. While the results clearly demonstrate a higher pH will provide favorable stability, it is desirable to have a final drug product pH at or close to physiological pH. Therefore, it is important to design a formulation that provides acceptable stability at or close to physiological pH.

Example 3

Photostability of Cangrelor in Solution

Impurity C is obtained through the formation of sulfoxide from a sulfide found in cangrelor and is therefore an oxidized form of cangrelor. Such oxidations are mediated by light (Liang et al. *J. Am. Chem. Soc.* 1983, 105, 4717).

The photostability of cangrelor was measured to evaluate the potential for light mediated degradation. Namely, solid cangrelor was placed in two quartz cuvettes. Both cuvettes were placed in a chamber and exposed to a combination of 320-400 nM (near UV) and 400-800 nM (visible) light for a total of $7.8 \times 10^6$ LUX hours and 221 watt hours/m$^2$, but one cuvette was wrapped in aluminum foil. After 17 days, the levels of impurities in the sample were determined by reverse phase HPLC. In this study, the total level of impurities, initially at 0.8% (w/w) in this batch, was found to be at 4.3% (w/w) in the exposed sample and 1.2% (w/w) in the shielded sample. While the degradation of the unexposed sample accounts for degradation that is not light mediated, the higher rate of degradation in the exposed sample demonstrates the sensitivity of cangrelor to light mediated processes.

While this study is not representative of the conditions of storage of cangrelor in a quantitative way, it does show qualitatively that cangrelor is sensitive to conditions of exposure to air and light.

While the previous study demonstrated the need to protect cangrelor itself from light and air, a separate study was performed with the bulk formulation of cangrelor prepared as per the process described in the invention. The bulk formulation was dissolved at a concentration of 16.42 mg/mL and exposed to ordinary room lighting for 4, 8, and 24 hours and then analyzed for assay and impurities. Solution not exposed to light served as the control. The impurity levels were determined by reverse phase HPLC and presented in Table 3.

TABLE 3

Light stability data of Cangrelor bulk formulation

| Time Point (hour) | Cangrelor level (% initial) | | Impurities | Impurity level (% peak area) | |
| --- | --- | --- | --- | --- | --- |
| | Shielded from light | Exposed to light | | Shielded from light | Exposed to light |
| Initial | 100% | N/A | Impurity A | 0.13 | N/A |
| | | | Impurity B | <0.05 | N/A |
| 4 | 98.9 | 101.5 | Impurity A | 0.13 | 0.13 |
| | | | Impurity B | 0.06 | 0.06 |
| | | | Impurity C | NP | <0.05 |
| 8 | 100.7 | 100 | Impurity A | 0.14 | 0.14 |
| | | | Impurity B | 0.06 | 0.06 |
| | | | Impurity C | NP | 0.07 |
| 24 | 97.8 | 99.1 | Impurity A | 0.16 | 0.16 |
| | | | Impurity B | 0.06 | NP |
| | | | Impurity C | NP | 0.14 |

N/A - not applicable
NP - not present

In this study, even over the short duration of the experiment, it is clear that the level of impurity C increases over time. This clearly demonstrates that cangrelor is sensitive to photooxidation.

Example 4

Sensitivity of Cangrelor to Oxidation

The susceptibility of cangrelor to oxidation was evaluated by exposing cangrelor formulated in mannitol/sorbitol to 0.1% hydrogen peroxide for 1 h. The levels of cangrelor and impurity C (the oxidation product of cangrelor) were then measured by reverse-phase HPLC. Even under these relatively mild oxidative conditions, there was only 12.46±0.70% of cangrelor by peak area left after 1 h and 83.88±0.47% of impurity C had been produced by peak area.

This experiment shows that cangrelor is susceptible to oxidation and while these conditions are harsher than those brought by exposure to air, they demonstrate the need to keep cangrelor away from oxidants such as oxygen.

Example 5

Correlation of Stability with Moisture Level

The hygroscopicity of cangrelor tetrasodium has been measured using the dynamic vapor adsorption analysis method and cangrelor was determined to be hygroscopic. Given the fact that as seen in Examples 1 and 2, cangrelor is sensitive to hydrolysis, it was of interest to determine if absorbed moisture can cause degradation over time.

Vials of cangrelor were prepared through the lyophilization of cangrelor tetrasodium (57.72 mg per vial), mannitol (164.4 mg per vial) and sorbitol (54.3 mg per vial) in two batches. Batch A was lyophilized to a moisture content of 0.33% and batch B was lyophilized to a moisture content of 2.0%. The vials were sealed with a rubber cap, crimped and stored in one of four conditions: at 5° C. and ambient humidity, at 25° C. and 60% relative humidity, at 30° C. and 60% relative humidity and at 40° C. and 75% relative humidity. At specific time points ranging from 0-12 months, the levels of impurities were measured by reverse phase HPLC and the moisture levels were measured by Karl-Fischer titration. The values measured are reported in Table 4.

TABLE 4

Long term stability of cangrelor formulations

| Batch | Storage conditions (° C./% Relative Humidity) | Time (months) | Moisture level (% w/w) | Total impurities (% w/w) |
| --- | --- | --- | --- | --- |
| A | Initial | 0 | 0.33 | 0.18 |
| | 5/ambient | 3 | 0.36 | 0.19 |
| | | 6 | 0.53 | 0.18 |
| | | 9 | 0.58 | 0.19 |
| | | 12 | 0.74 | 0.18 |
| | 25/60 | 3 | 0.57 | 0.2 |
| | | 6 | 0.72 | 0.19 |
| | | 9 | 0.77 | 0.19 |
| | | 12 | 0.84 | 0.19 |
| | 30/60 | 3 | 0.62 | 0.2 |
| | | 6 | 0.68 | 0.21 |
| | | 9 | 0.75 | 0.22 |
| | | 12 | 0.82 | 0.23 |
| | 40/75 | 3 | 0.66 | 0.27 |
| | | 6 | 0.78 | 0.37 |
| | | 9 | 1.08 | 0.45 |
| | | 12 | 1.01 | 0.70 |
| B | Initial | 0 | 2.00 | 0.18 |
| | 5/ambient | 3 | 1.80 | 0.19 |
| | | 6 | 2.03 | 0.18 |
| | | 9 | 2.21 | 0.18 |
| | | 12 | 2.18 | 0.18 |
| | 25/60 | 3 | 2.06 | 0.19 |
| | | 6 | 1.93 | 0.22 |
| | | 9 | 2.11 | 0.24 |
| | | 12 | 2.08 | 0.25 |
| | 30/60 | 3 | 1.94 | 0.24 |
| | | 6 | 1.86 | 0.28 |
| | | 9 | 2.30 | 0.31 |
| | | 12 | 1.90 | 0.31 |
| | 40/75 | 3 | 1.81 | 0.52 |
| | | 6 | 1.78 | 3.64 |
| | | 9 | 2.34 | 5.80 |
| | | 12 | 2.05 | 5.75 |

This data, and in particular the values measured at 40° C. and 75% relative humidity, clearly demonstrates that even in sealed lyophilization vials, the cangrelor formulation slowly absorbs moisture and that, in parallel, the quantity of impurities rise. It shows that a process to exclude moisture is necessary to produce a cangrelor composition that can be stored for a period and remain useable.

Example 6

Stability of Cangrelor Produced and Stored Under Conditions of the Invention

Cangrelor batches A-E (Table 5) were produced according to the invention. Their pH was adjusted to 8.5 prior to lyophilization and they were stored in glass vials stoppered with a stopper specifically selected for its ability to retain as little moisture as possible after autoclaving and after drying for 8 h at 105° C. Together with cangrelor (50 mg of the tetrasodium salt per vial), excipients mannitol (164.4 mg per vial) and sorbitol (54.3 mg per vial) were included in the formulation.

Cangrelor lots API A-B are cangrelor tetrasodium. They were stored in double polyethylene bags in HDPE pails.

These lots were placed in storage at 25° C. and 60% relative humidity and at the time points indicated in Table 5, aliquots were removed and the level of impurities was measured by either reverse phase HPLC or by ion chromatography for impurity E. In addition their moisture content was determined by Karl-Fischer titration. All these data are reported in Table 5. In addition, throughout the storage period, the pH of 1% w/v solutions of the material in batches A-E were measured and remained at between 8.4 and 8.8 throughout.

TABLE 5

Long term stability of cangrelor formulations

| Lot | Analyte | Analyte concentration (% w/w) over time (months) | | | | | | | | | |
|---|---|---|---|---|---|---|---|---|---|---|---|
| | | Initial | 1 | 3 | 6 | 9 | 12 | 18 | 24 | 30 | 36 |
| Batch A | Impurity A | 0.25 | 0.25 | 0.26 | 0.26 | 0.26 | 0.27 | 0.28 | 0.29 | 0.30 | 0.31 |
| | Impurity B | 0.06 | 0.06 | 0.06 | 0.06 | 0.06 | 0.06 | 0.07 | 0.06 | 0.06 | 0.07 |
| | Impurity C | <0.05 | <0.05 | <0.05 | <0.05 | <0.05 | <0.05 | 0.05 | <0.05 | <0.05 | 0.05 |
| | Impurity E | 0.09 | 0.10 | 0.10 | 0.10 | 0.08 | 0.08 | 0.09 | 0.08 | 0.09 | 0.09 |
| | Total impurities | 0.70 | 0.70 | 0.70 | 0.80 | 0.66 | 0.67 | 0.70 | 0.70 | 0.80 | 0.80 |
| | Moisture | 0.3 | 0.4 | 0.4 | 0.4 | 0.4 | 0.6 | 0.6 | 0.6 | 0.8 | 0.8 |
| Batch B | Impurity A | 0.13 | 0.13 | 0.12 | 0.14 | 0.14 | 0.14 | 0.19 | 0.16 | 0.19 | — |
| | Impurity B | <0.05 | <0.05 | <0.05 | <0.05 | <0.05 | <0.05 | <0.05 | <0.05 | 0.0 | — |
| | Impurity C | <0.05 | <0.05 | <0.05 | <0.05 | <0.05 | <0.05 | <0.05 | 0.05 | 0.06 | — |
| | Impurity E | <0.05 | <0.05 | <0.05 | <0.05 | <0.05 | 0.05 | <0.05 | <0.05 | 0.04 | — |
| | Total impurities | 0.13 | 0.13 | 0.13 | 0.14 | 0.14 | 0.19 | 0.19 | 0.36 | 0.40 | — |
| | Moisture | 0.3 | 0.3 | 0.4 | 0.4 | 0.5 | 0.5 | 0.5 | 0.6 | 0.7 | — |
| Batch C | Impurity A | 0.10 | 0.15 | 0.15 | 0.15 | 0.16 | 0.16 | 0.17 | — | — | — |
| | Impurity B | <0.05 | <0.05 | <0.05 | 0.05 | <0.05 | <0.05 | 0.05 | — | — | — |
| | Impurity C | <0.05 | <0.05 | <0.05 | 0.05 | 0.04 | 0.05 | 0.06 | — | — | — |
| | Impurity E | <0.05 | <0.05 | <0.05 | 0.05 | <0.05 | <0.05 | <0.05 | — | — | — |
| | Total impurities | 0.10 | 0.15 | 0.15 | 0.30 | 0.21 | 0.21 | 0.30 | — | — | — |
| | Moisture | 0.3 | 0.4 | 0.4 | 0.5 | 0.5 | 0.7 | 1.1 | — | — | — |
| Batch D | Impurity A | ND | 0.10 | 0.12 | 0.13 | 0.14 | 0.13 | 0.13 | 0.16 | — | — |
| | Impurity B | <0.05 | — | — | 0.05 | 0.05 | 0.05 | — | 0.05 | — | — |
| | Impurity C | <0.05 | <0.05 | <0.05 | <0.05 | ND | ND | <0.05 | 0.05 | — | — |
| | Impurity E | <0.05 | <0.05 | <0.05 | <0.05 | <0.05 | <0.05 | <0.05 | <0.05 | — | — |
| | Total impurities | 0.50 | 0.20 | 0.20 | 0.20 | 0.20 | 0.20 | 0.30 | 0.30 | — | — |
| | Moisture | 0.3 | 0.4 | 0.3 | 0.5 | 0.4 | 0.6 | 0.6 | 0.7 | — | — |
| Batch E | Impurity A | ND | 0.10 | 0.11 | 0.12 | 0.14 | 0.11 | 0.12 | — | — | — |
| | Impurity B | — | — | 0.05 | 0.05 | 0.05 | 0.05 | 0.05 | — | — | — |
| | Impurity C | — | — | <0.05 | ND | ND | 0.05 | 0.05 | — | — | — |
| | Impurity E | <0.05 | <0.05 | <0.05 | <0.05 | <0.05 | <0.05 | <0.05 | — | — | — |
| | Total. impurities | 0.10 | — | 0.20 | 0.20 | 0.20 | 0.20 | 0.40 | — | — | — |
| | Moisture | 0.4 | — | 0.4 | 0.4 | 0.7 | 0.7 | 0.7 | | | |
| API A | Impurity A | 0.15 | 0.28 | 0.47 | — | — | — | — | — | — | — |
| | Impurity B | 0.11 | 0.22 | 0.33 | — | — | — | — | — | — | — |
| | Impurity C | — | — | — | — | — | — | — | — | — | — |
| | Impurity E | 0.06 | 0.08 | 0.11 | — | — | — | — | — | — | — |
| | Total impurities | 0.70 | 1.10 | 1.40 | — | — | — | — | — | — | — |
| | Moisture | 4.3 | 7.7 | 11.3 | — | — | — | — | — | — | — |
| API B | Impurity A | 0.31 | 0.36 | 0.51 | 0.70 | — | — | — | — | — | — |
| | Impurity B | 0.11 | 0.19 | 0.32 | 0.48 | — | — | — | — | — | — |
| | Impurity C | <0.05 | 0.06 | 0.08 | 0.19 | — | — | — | — | — | — |
| | Impurity E - | — | — | — | — | — | — | — | — | — | — |
| | Total impurities | 0.80 | 1.10 | 1.50 | 1.90 | — | — | — | — | — | — |
| | Moisture | 7.0 | 6.9 | 9.9 | 11.6 | — | — | — | — | — | — |

These data demonstrate that batches A-E produced by the process disclosed in the invention remain stable for up to 36 months without either significant degradation or significant increase in moisture content. In comparison, lots API A and API B rapidly concentrate moisture and display significant degradation over time.

These data support the use of the process described in the invention for the generation of high purity cangrelor formulations that can be stored for a long period of time and be useable in patients.

What is claimed is:

1. A pharmaceutical formulation comprising high purity cangrelor, or a salt thereof, as an active ingredient and one or more pharmaceutically acceptable excipients,
    wherein the pharmaceutical formulation has less than about 2.0% moisture on a weight basis,
    wherein the pharmaceutical formulation has a pH of between about 7.0 and about 9.5,
    wherein the high purity cangrelor or salt thereof has a combined total of selected hydrolysis and oxidation degradants of cangrelor not exceeding about 1.5% by weight of the high purity cangrelor, and
    wherein the selected hydrolysis and oxidation degradants are one or more members selected from the group consisting of:
    impurity A

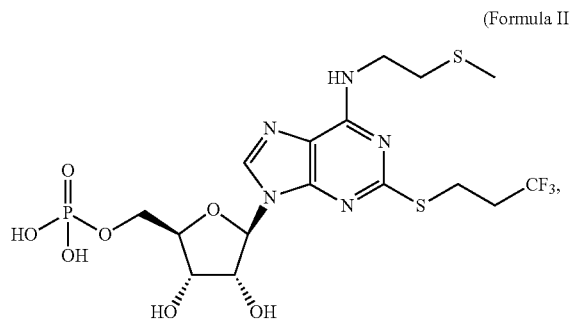
(Formula II)

impurity B

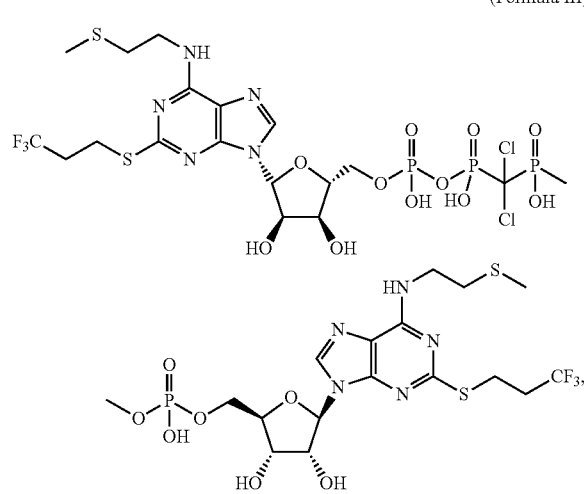
(Formula III)

impurity C

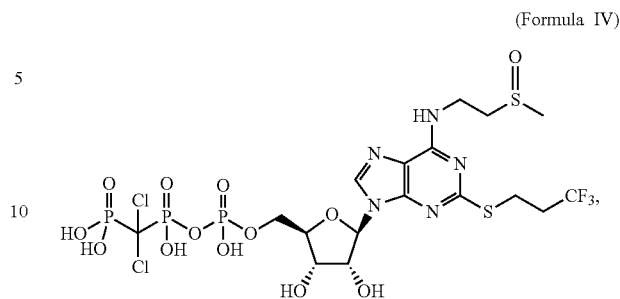
(Formula IV)

impurity D

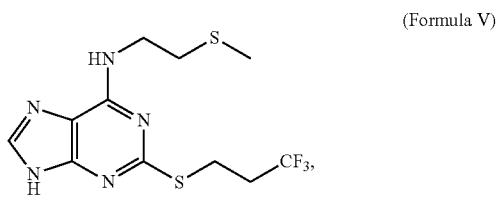 [SMILES: CSCCNc1nc(SCCC(F)(F)F)nc2[nH]cnc12]
(Formula V)

and
impurity E

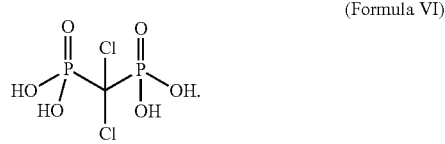 [SMILES: O=P(O)(O)C(Cl)(Cl)P(=O)(O)O]
(Formula VI)

2. The pharmaceutical formulation of claim 1, wherein the combined total of selected hydrolysis and oxidation degradants of cangrelor does not exceed about 1.3% by weight of the high purity cangrelor.

3. The pharmaceutical formulation of claim 1, wherein the amount of impurity A is less than about 0.5% by weight, the amount of impurity B present is less than about 0.2% by weight, the amount of impurity C is less than about 0.3% by weight, the amount of impurity D is less than about 0.2% by weight, and the amount of impurity E is less than about 0.5% by weight of the high purity cangrelor.

4. The pharmaceutical formulation of claim 1, wherein the maximum impurity level of impurities A and D is each less than about 0.5% by weight of the high purity cangrelor.

5. The pharmaceutical formulation of claim 1, wherein the pharmaceutically acceptable excipient is a polyol.

6. The pharmaceutical formulation of claim 1, wherein the pharmaceutically acceptable excipients are mannitol and sorbitol.

7. The pharmaceutical formulation of claim 1, wherein the pharmaceutical formulation comprises about 16-21% high purity cangrelor and about 84-79% of the one or more pharmaceutically acceptable excipients, by weight of the pharmaceutical formulation.

8. A sealed vessel containing the pharmaceutical formulation of claim 1 under a chemically inert dry gas.

9. The sealed vessel of claim 8, wherein the chemically inert dry gas is nitrogen or argon.

10. The sealed vessel of claim 8, wherein moisture in the pharmaceutical formulation remains below 5.0% on a weight basis over a period of at least about 6 months.

11. The sealed vessel of claim 8, wherein after a period of about 12 months, the pharmaceutical formulation is characterized by a pH of between about 7.0 and 9.5 for a 1% solution by weight, an amount of moisture less than about 5% on a weight basis, a maximum level of the impurities A, B, C and D not exceeding about 1% each by weight of the high purity cangrelor and a maximum level of impurity E not exceeding about 0.5% by weight of the high purity cangrelor.

12. The sealed vessel of claim 8, wherein after a period of about 12 months, the pharmaceutical formulation is characterized by a pH of between about 7.0 and 9.5 for a 1% solution by weight, an amount of moisture less than about 5% on a weight basis, and a maximum combined level of impurities A, B, C, D and E not exceeding about 5% by weight of the high purity cangrelor.

13. The sealed vessel of claim 8, wherein after a period of about 12 months, the pharmaceutical formulation is characterized by a pH of between about 7.0 and 9.5 for a 1% solution by weight, an amount of moisture less than about 5% on a weight basis, and a maximum combined level of impurities A, B, C, D and E not exceeding about 2% by weight of the high purity cangrelor.

14. A pharmaceutical formulation consisting of high purity cangrelor, or a salt thereof, as an active ingredient and mannitol and/or sorbitol as a pharmaceutically acceptable excipient,
wherein the pharmaceutical formulation has less than about 2.0% moisture on a weight basis,
wherein the pharmaceutical formulation has a pH of between about 7.0 and about 9.5,
wherein the high purity cangrelor or salt thereof has a combined total of selected hydrolysis and oxidation degradants of cangrelor not exceeding about 1.5% by weight of the high purity cangrelor, and
wherein the selected hydrolysis and oxidation degradants are one or more members selected from the group consisting:

impurity A (Formula II)

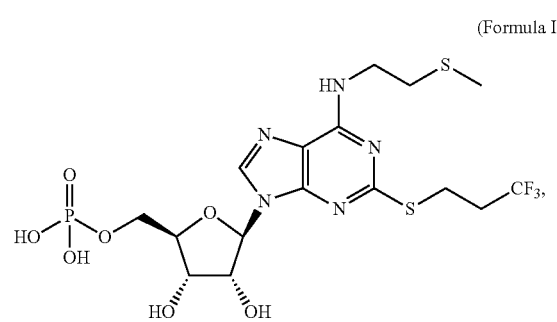 [SMILES: CSCCNc1nc(SCCC(F)(F)F)nc2c1ncn2[C@@H]1O[C@H](COP(=O)(O)O)[C@@H](O)[C@H]1O]

impurity B impurity C (Formula IV)

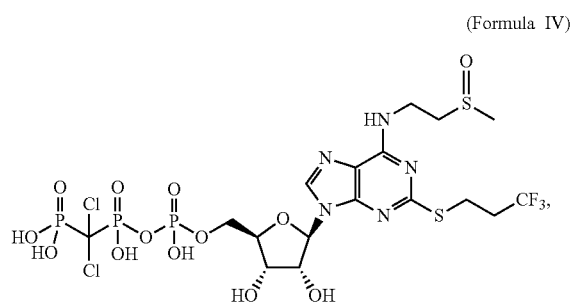 [SMILES: CS(=O)CCNc1nc(SCCC(F)(F)F)nc2c1ncn2[C@@H]1O[C@H](COP(=O)(O)OP(=O)(O)C(Cl)(Cl)P(=O)(O)O)[C@@H](O)[C@H]1O]

impurity D (Formula V)

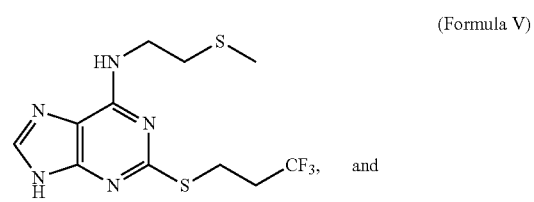 [SMILES: CSCCNc1nc(SCCC(F)(F)F)nc2[nH]cnc12 ; "and"]
and impurity E (Formula VI)

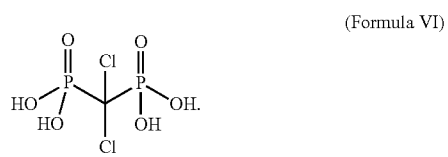 [SMILES: O=P(O)(O)C(Cl)(Cl)P(=O)(O)O]

15. The pharmaceutical formulation of claim 14, wherein the combined total of selected hydrolysis and oxidation degradants of cangrelor does not exceed about 1.3% by weight of the high purity cangrelor.

16. The pharmaceutical formulation of claim 14, wherein the amount of impurity A is less than about 0.5% by weight, the amount of impurity B present is less than about 0.2% by weight, the amount of impurity C is less than about 0.3% by weight, the amount of impurity D is less than about 0.2% by weight, and the amount of impurity E is less than about 0.5% by weight of the high purity cangrelor.

17. The pharmaceutical formulation of claim 14, wherein the maximum impurity level of impurities A and D is each less than about 0.5% by weight of the high purity cangrelor.

(Formula III)

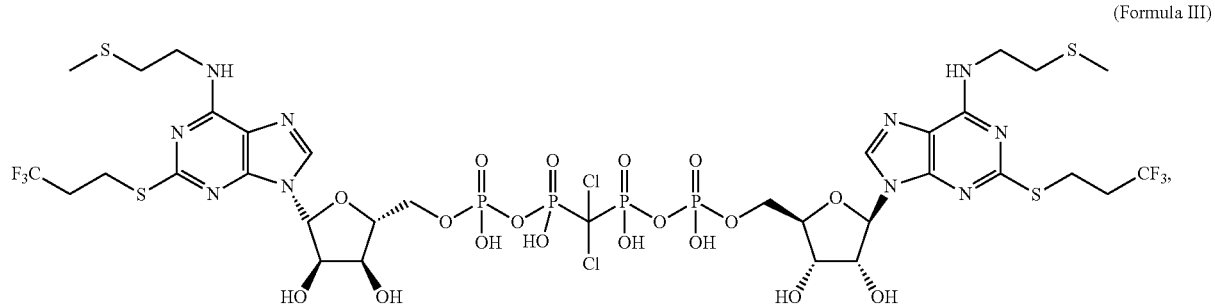

18. The pharmaceutical formulation of claim 14, wherein the pharmaceutically acceptable excipient is a polyol.

19. The pharmaceutical formulation of claim 14, wherein the pharmaceutically acceptable excipients are mannitol and sorbitol.

20. The pharmaceutical formulation of claim 14, wherein the pharmaceutical formulation comprises about 16-21% high purity cangrelor and about 84-79% of the one or more pharmaceutically acceptable excipients, by weight of the pharmaceutical formulation.

21. A sealed vessel containing the pharmaceutical formulation of claim 14 under a chemically inert dry gas.

22. The sealed vessel of claim 21, wherein the chemically inert dry gas is nitrogen or argon.

23. The sealed vessel of claim 21, wherein moisture in the pharmaceutical formulation remains below 5.0% on a weight basis over a period of at least about 6 months.

24. The sealed vessel of claim 21, wherein after a period of about 12 months, the pharmaceutical formulation is characterized by a pH of between about 7.0 and 9.5 for a 1% solution by weight, an amount of moisture less than about 5% on a weight basis, a maximum level of the impurities A, B, C and D not exceeding about 1% each by weight of the high purity cangrelor and a maximum level of impurity E not exceeding about 0.5% by weight of the high purity cangrelor.

25. The sealed vessel of claim 21, wherein after a period of about 12 months, the pharmaceutical formulation is characterized by a pH of between about 7.0 and 9.5 for a 1% solution by weight, an amount of moisture less than about 5% on a weight basis, and a maximum combined level of impurities A, B, C, D and E not exceeding about 5% by weight of the high purity cangrelor.

26. The sealed vessel of claim 21, wherein after a period of about 12 months, the pharmaceutical formulation is characterized by a pH of between about 7.0 and 9.5 for a 1% solution by weight, an amount of moisture less than about 5% on a weight basis, and a maximum combined level of impurities A, B, C, D and E not exceeding about 2% by weight of the high purity cangrelor.

* * * * *